US010215662B2

(12) United States Patent
Newman et al.

(10) Patent No.: US 10,215,662 B2
(45) Date of Patent: *Feb. 26, 2019

(54) SYSTEMS AND METHODS FOR THE INSPECTION OF CONTACT LENSES

(71) Applicant: MENICON SINGAPORE PTE LTD., Singapore (SG)

(72) Inventors: Stephen Donald Newman, Singapore (SG); Hiroyama Oyama, Erlangen (DE); Johannes Pfund, Erlangen (DE); Juergen Lamprecht, Erlangen (DE)

(73) Assignee: MENICON SINGAPORE PTE LTD., Singapore (SG)

(*) Notice: Subject to any disclaimer, the term of this patent is extended or adjusted under 35 U.S.C. 154(b) by 0 days.

This patent is subject to a terminal disclaimer.

(21) Appl. No.: 15/792,568

(22) Filed: Oct. 24, 2017

(65) Prior Publication Data

US 2018/0045604 A1 Feb. 15, 2018

Related U.S. Application Data

(63) Continuation of application No. 14/400,275, filed as application No. PCT/SG2013/000187 on May 10, 2013, now Pat. No. 9,797,803.

(30) Foreign Application Priority Data

May 10, 2012 (SG) .................................. 201203439

(51) Int. Cl.
*G01M 11/02* (2006.01)
*G01N 21/88* (2006.01)
(Continued)

(52) U.S. Cl.
CPC ..... *G01M 11/0214* (2013.01); *G01N 21/8803* (2013.01); *G01N 21/958* (2013.01); *G01N 21/03* (2013.01); *G01N 2021/9583* (2013.01)

(58) Field of Classification Search
CPC ....... G01M 11/0214; G01N 2021/9583; G01N 21/03; G01N 21/8803; G01N 21/958
(Continued)

(56) References Cited

U.S. PATENT DOCUMENTS 4,665,624 A * 5/1987 Wodis ...................... G01B 5/20
33/507
5,995,213 A * 11/1999 Davis ................. G01M 11/0207
356/124

(Continued)

FOREIGN PATENT DOCUMENTS

EP 0491663 A1 6/1992
EP 1674822 A1 6/2006
(Continued)

OTHER PUBLICATIONS

PCT International Search Report for PCT International Patent Application No. PCT/SG2013/000187, dated Aug. 7, 2013.
(Continued)

*Primary Examiner* — Tri T Ton
(74) *Attorney, Agent, or Firm* — Dorsey & Whitney LLP

(57) ABSTRACT

An apparatus for inspecting lenses includes an inspection system including an open cuvette, a communicatively coupled CT measurement device, and a user interface communicatively coupled to the inspection system. According to one embodiment, the lens inspection system provides a single instrument for inspecting the quality of a lens, thereby minimizing the transference of the lens from one inspection component to another.

19 Claims, 24 Drawing Sheets

(51) Int. Cl.
*G01N 21/958* (2006.01)
*G01N 21/03* (2006.01)

(58) Field of Classification Search
USPC .................................................. 356/123–137
See application file for complete search history.

(56) References Cited

U.S. PATENT DOCUMENTS

| | | | | |
|---|---|---|---|---|
| 9,797,803 | B2* | 10/2017 | Newman | G01N 21/8803 |
| 2002/0163638 | A1* | 11/2002 | Biel | G01M 11/0278 |
| | | | | 356/239.2 |
| 2006/0132761 | A1* | 6/2006 | Hall | G01M 11/02 |
| | | | | 356/244 |
| 2007/0291258 | A1* | 12/2007 | Divo | G01M 11/0235 |
| | | | | 356/124 |
| 2012/0019813 | A1* | 1/2012 | Yoshitake | G01M 11/0207 |
| | | | | 356/213 |

FOREIGN PATENT DOCUMENTS

| | | |
|---|---|---|
| JP | 2011222966 A | 11/2011 |
| WO | 2008080074 | 7/2008 |

OTHER PUBLICATIONS

Supplementary European Search Report for Corresponding European Patent Application No. 13787245.3, dated Dec. 17, 2015.
Second Office Action for European Patent Application No. 13787245.3, dated Jul. 12, 2018 (5 pages).

* cited by examiner

BC ≈ 8.6mm:    Δs = 5μ  => ΔR = 20μ

BC = 30mm:    Δs = 5μ  => ΔR = 350μ

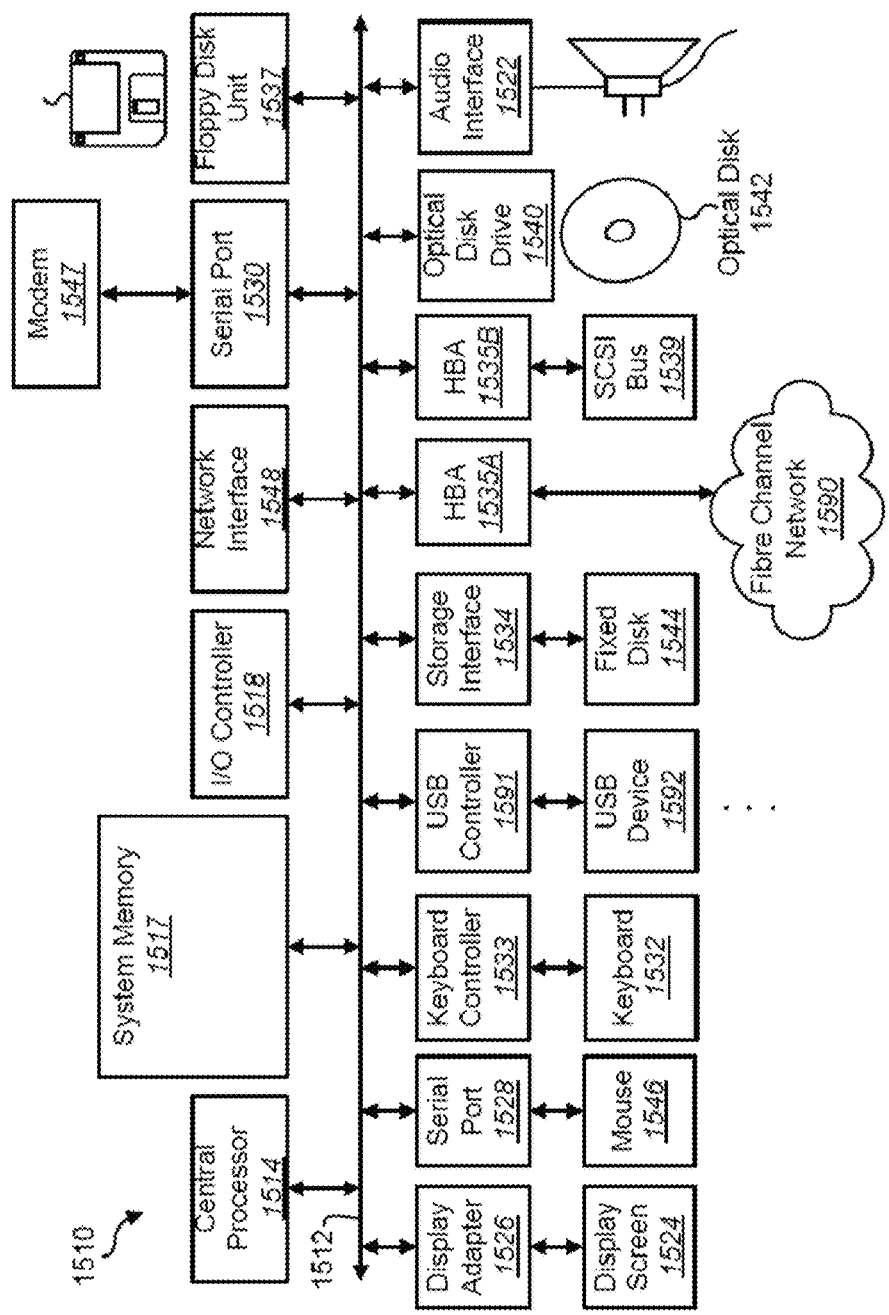

SYSTEMS AND METHODS FOR THE INSPECTION OF CONTACT LENSES

RELATED APPLICATIONS

The present application is a continuation of U.S. application Ser. No. 14/400,275, filed Nov. 10, 2014, now U.S. Pat. No. 9,797,803, which is a National Stage Entry of PCT Application No. PCT/SG2013/000187 and claims priority to Singapore Patent Application No. 201203439-3, filed May 10, 2012, now Singapore Patent No. 195400, the entire disclosures of which are hereby incorporated by reference in their entireties.

BACKGROUND

In recent decades, contact lenses have become a preferential alternative to other eyesight correction methods. Due to their increased popularity, it has become mandatory that contact lenses be manufactured on a large scale in order to meet consumer demand. Further, these lenses are required to be precision manufactured with low tolerances in order to provide a suitable and effective corrective lens.

The polymerization casting of axially symmetrical articles, such as contact lenses, may be performed by using a spin casting process. Spin casting has proven to be an effective way to mass produce contact lenses. In this process, a controlled quantity of a polymerizable liquid is placed into an open mold, which is then rotated about its vertical axis at a rotational speed sufficient to produce a centrifugal force that causes a radially outward displacement of the polymerizable liquid. By maintaining a controlled rotation rate, the centrifugal force caused by the rotation will cause the polymerizable liquid to adopt a generally concave shape. Once the polymerizable liquid has attained an equilibrium shape, polymerization of the liquid can be effected by any suitable means, such as heat or exposure to actinic radiation (i.e. ultraviolet light) so as to produce a solid polymeric contact lens.

The open mold used in a spin casting process is typically characterized by an outer cylindrical wall and a mold comprising an exposed concave molding cavity. The shape of the molding cavity will typically define the shape of the front surface of the finished contact lens, and may contain such desired elements as lenticulating curves, toric curves, non-spherical curves and other such features or shapes aimed at interacting with the eye, its optical processes, or eyelids in a predetermined manner.

The shape factor of the posterior or back surface of the lens is determined predominantly by the angular speed of rotation, as well as other factors such as the surface tension of the polymerizable liquid, and the acceleration due to gravity.

During the manufacture of contact lenses, the polymer is typically polymerized in a spin tube. The spin tube must be able to both present an accurate and straight inner bore for the molds and must spin around its own vertical axis with minimal run out of polymerizable liquid and minimal vibration within the system. Inconsistencies in the production of spin-cast contact lenses may be introduced by any number of manufacturing elements. For example, variance in the run out of the spin tube may affect the final contact lens. Additionally, inaccurate mounting of the spin tub into the rotation mount may introduce inaccuracies that affect the contact lens produced. Additionally, contaminants may be inadvertently introduced or system vibrations may generate a product that lacks sufficient precision (e.g. a contact lens with undesirable imperfections or defects). Furthermore, removal of the resultant lens from its mold may introduce rips and other defects to the lens.

In order to assure constant quality of the contact lenses, provisions are in place for automatic inspection of the contact lenses using industrial image processing methods. In image processing, the lenses are tested both in the mould halves and at the vacuum grips. An image processing method of this kind is described for example in EP patent 491663. Of course, not all defective contact lenses can be detected by this type of inspection, or nominal defects are established, such as bubbles formed by water spillages, which however illustrate artifacts. Furthermore, automated inspection systems are ill equipped to identify artifacts on the lens that may not be lens defects, but rather system contamination, such as dust specs and/or fibers. By having to sort out the perfect lenses, the yield is reduced, which has a negative effect on balancing the costs.

In order to reduce the negative effect of automated inspection systems, many current systems incorporate manual inspection of the lens. However, in order to manually inspect multiple aspects of a lens, the lens is transferred to multiple instruments. The multiple transference of the lens can actually damage or deform the lens as part of the inspection process. Consequently, this traditional manual inspection system generally causes an artificially inflated rate of lens loss and waste. This increased lens loss during the inspection process is particularly troublesome in a prescription lab which is manufacturing a one-off prescription lens for a particular individual.

In other words, traditional inspection systems incorporate multiple instruments, thereby introducing the possibility of lens damage during transference between instruments. Additionally, the increase in damage to the lenses generally requires the use of additional lenses. Furthermore, traditional systems often introduce drying of the lens which potentially changes the dimensions of the very lenses you are measuring. This change in lens dimensions via the process is counterintuitive when trying to measure an object in a static state.

SUMMARY

According to one exemplary embodiment, an apparatus for the inspection of contact lenses provides for a more flexible approach to the inspection of ophthalmic products, allows for faster and more efficient inspection, can improve the objectivity of inspection outcomes irrespective of operator skill or experience, while providing for a single inspection system that can provide a means to fully inspect and grade lenses within a controlled and efficient audit station.

According to one exemplary embodiment, the present exemplary system provides an inspection system that includes a measurement device communicatively coupled to a CT measurement instrument. The Measurement device includes a cuvette designed to provide a fully wet measurement environment that provides closed cuvette properties. According to this embodiment, the cuvette includes a magnetic cuvette positioning and retention system that eliminates the need for fasteners in the actual cuvette. Additionally, the exemplary cuvette includes anti-schlieren and vibration/pulse control properties, at least in the form of baffle plates and mixing plates that homogenize the temperature gradients in the cuvette.

Additionally, according to one exemplary embodiment, the present exemplary lens inspection system includes a base curve measurement system that incorporates raytracing in conjunction with profilometry and sagittal evaluation. The exemplary system incorporates multiple and sequential lighting conditions to provide the optimal views for accurately identifying lens imperfections. Additionally, according to one exemplary embodiment, the present exemplary system incorporates a color interpretation module that provides for accurate detection of iron based materials in the lens under inspection.

Furthermore, according to one exemplary embodiment, the present exemplary lens inspection systems and methods include a system that incorporates both human qualification and computer quantification. The human qualification is enabled, according to one exemplary embodiment, via an intuitive touch screen inspector interface. This provides for objective LOT grading and human qualification and computer quantification based inspection.

BRIEF DESCRIPTION OF THE DRAWINGS

The accompanying drawings illustrate various embodiments of the principles described herein and are a part of the specification. The illustrated embodiments are merely examples and do not limit the scope of the claims.

FIG. 14 depicts a block diagram of a computer system suitable for implementing the present systems and methods.

Throughout the drawings, identical reference numbers designate similar, but not necessarily identical, elements.

DETAILED DESCRIPTION

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "an embodiment," "an example" or similar language means that a particular feature, structure, or characteristic described in connection with the embodiment or example is included in at least that one embodiment, but not necessarily in other embodiments. The various instances of the phrase "in one embodiment" or similar phrases in various places in the specification are not necessarily all referring to the same embodiment.

The present exemplary system and methods are configured for the inspection and grading of ophthalmic products. More specifically, according to one exemplary embodiment, the present exemplary systems and methods are configured for the efficient and accurate inspection of contact lenses. While the present specification will describe the exemplary inspection system, for ease of explanation only, as being used to inspect the quality of newly manufactured contact lenses, it will be understood that the present exemplary system may be used to visually inspect any number of ophthalmic products.

Overall System

Figure 1A:
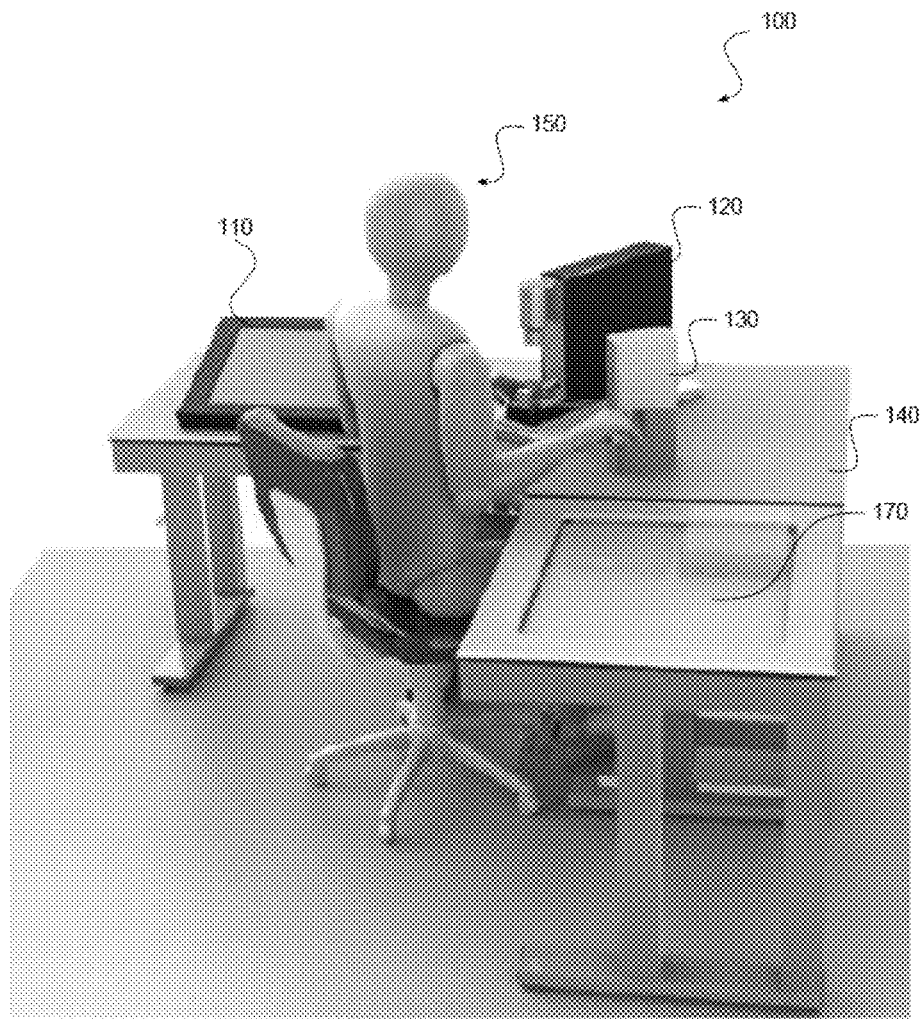
FIG. 1A is a perspective view of a user inspecting a lens with a lens inspection system, according to an embodiment of the present exemplary system and method.

FIG. 1 A is a perspective view of a user inspecting a lens with a lens inspection system, according to an embodiment of the present exemplary system and method. As illustrated in FIG. 1A, the present exemplary inspection system 100 includes a measurement device 120 communicatively coupled to a pen display 110 and a center thickness (CT) gauge 130. The exemplary inspection system 100 is disposed, according to one exemplary embodiment, on a stable support structure 140 for easy and reliable use by a user 150, which stable support structure may include a tray table 170 having a highly resistant surface.

Figure 1B:
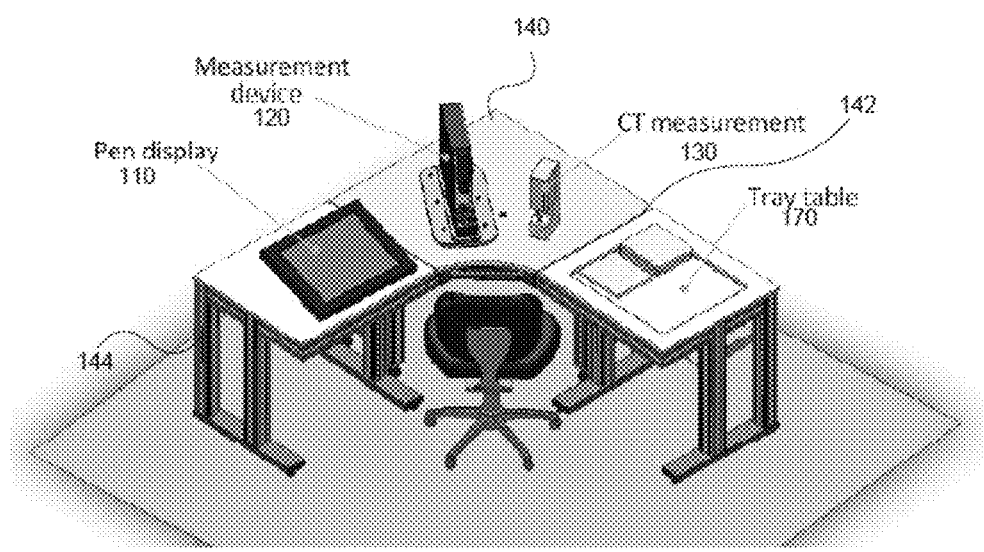
FIG. 1B is a perspective view of the lens inspection system of FIG. 1A, according to one embodiment of the present exemplary system and method.

FIG. 1B further provides a perspective view of the lens inspection system 100 of FIG. 1A without the user 150, for ease of view, according to one embodiment of the present exemplary system and method. As shown in FIG. 1B, the exemplary inspection system 100 includes a user interface, which may be in the form of a pen display 110, and a CT gauge 130, communicatively coupled to a measurement device 120. The support structure 140 structurally supporting the lens inspection system 100 may include any number of features aimed at increasing the accuracy of measurements and reducing the introduction of image degrading environmental variances including, but in no way limited to, separated tables 142 to reduce the transfer of vibrations, a weighty framework 144 to reduce static and transient vibrations, frames filled with sand, spikes on the floor, and any other features or devices configured to reduce standard waves and vibrational effects.

As mentioned above, the present exemplary system and method are configured to provide an increased order of inspection accuracy than a traditional system, while reducing inspection time, reducing user training time, and greatly reducing the occurrences of lens transference during inspection. Further details of the components of the exemplary lens inspection system 100 are provided below with reference to the figures.

Cuvette System

According to one exemplary embodiment, the present exemplary inspection system 100 is a single integrated system that includes an open cuvette 200 that facilitates the measurement of the lens under test 270 inside the cuvette without physically touching or transference of the lens. According to one exemplary embodiment, the open cuvette 200 facilitates the measurement of all parameters required by the International Organization for Standardization (ISO) except for CT. Consequently, according to the present exemplary method, the CT of the lens under test 270 is measured last, just before the lens under test is discarded or placed in a vial. According to the present exemplary method, as described in further detail below with reference to FIGS. 10A-11, the CT measurement is determined and fed back into the measurement device 120, via any number of wired or wireless communication features, to determine the base curve of the lens under test 270. Alternatively, all parameters required by ISO including CT may be obtained through the open cuvette 200. According to this exemplary embodiment, the CT of the lens may be determined while in the open cuvette 200 via optical means such as profilometry or the like.

Continuing with FIGS. 2A-2F, exemplary views of a lens cuvette 200 are illustrated, according to various embodiments of the present exemplary system and method. As illustrated, the lens cuvette 200 is disposed on a cuvette mounting base 430 of the inspection system 100 during use. According to one exemplary embodiment, the cuvette 200 includes an open top portion 201 that facilitates the insertion of a lens under test 270 into the cuvette. Additionally, the open top portion 201 of the exemplary cuvette 200 facilitates manipulation of the lens under test 270 with a pair of tweezers or other device during inspection.

As illustrated, the cuvette 200 includes a sensor mount 250 for positioning a thermal probe and/or other sensors in the saline contained within the cuvette with the lens under test 270. Additionally, the exemplary cuvette 200 includes a number of sidewalls 260 defining the interior of the cuvette 200 for the housing of the saline and lens under test 270. As shown, a number of light apertures 280, lenses 282, and measurement apertures 281 may be defined by the side wall 260 to facilitate the positioning, lighting, inspection, and imaging of the lens under test 270, as will be described in further detail below.

The incorporation of an open cuvette 200 with a closed based visual system provides a number of benefits to the present exemplary system. Traditional closed cuvettes are small, narrow capillary based systems where a lens is inserted. The closed cuvette system is often used because it provides a static state for inspection of the lens. The space in traditional cuvettes is such that a lens just fits inside without extra space. Once packaged, the lens would remain in the cuvette until opened by an inspection lab. However, manipulation during the inspection of a lens in a traditional closed cuvette could not be made.

In contrast, the present exemplary cuvette 200 allows for rapid insertion and inspection of a lens, while allowing for high levels of flexibility in touching the lens, moving the lens, repositioning the lens, manipulating the lens to determine if there is a particle on the lens during inspection that will float off. Additionally, the present cuvette still offers a completely static measuring environment similar to a closed cuvette system.

More specifically, the static measuring environment of the present cuvette 600 is provided via the saline orifices 286, inlays 240 disposed within the testing area, and a dynamically adjustable pump system, as described in further detail below. As illustrated in FIGS. 2C-2F, a number of saline orifices 286 may be formed in the cuvette 200 to facilitate the introduction of saline into the interior of the cuvette defined by the sidewalls 260. According to one exemplary embodiment, illustrated in FIG. 3, a pump 300 is incorporated to circulate saline into the cuvette 200. According to the present exemplary embodiment, the pump 300 is configured to be effective in moving the saline through a filter to keep the saline clean. However, as illustrated in FIG. 3, the pump 300 and the corresponding configuration is configured to controllably stop the flow of saline into the cuvette 200 at an instant to eliminate the flow of saline in the wet cell of the cuvette 200 during the measurement. In other words, to maximize precision of the measurements taken by the present exemplary measuring device 120, the saline contained within the cuvette 200 is completely still for the split second that the lens under test 270 is actually being measured.

As shown in FIG. 3, the pump is fluidly coupled to the cuvette 200 via the saline orifices 286. While the present exemplary system is described as pumping saline into the cuvette 200 during inspection, it will be recognized that any acceptable fluid may be used for hydration of the wet cell of the cuvette 200. As illustrated, the pump 300 provides saline to the cuvette 200 through an input valve 320 and saline is returned to the pump 300 via an output valve 330. Additionally, a bypass 310 fluidly communicates with the input and output lines associated with the pump 300. During operation, when a test of a lens under test 270 is to be made, the bypass 310 is opened and the input valve 320 and output valve 330 are closed. Consequently, the saline contained in the cuvette maintains static and free of flow for precise measurement. Additionally, the pump 300 may continue operation as the saline exiting the pump 300 is returned via the closed loop created by the bypass to maintain constancy of temperature. After the measurement is concluded, the bypass 310 closes and the input valve 320 and output valve 330 are actuated to allow the filtering flow of the saline to continue.

Due to this configuration, the microsecond that the imaging takes place, the saline has a pulsing effect and is absolutely static. Consequently, a closed cuvette effect is experienced within the cuvette 200. The top and bottom of the cuvette 200 are effectively closed by the surface of the saline and the sides of the cuvette are shut as well because the saline is no longer flowing, resulting in an open cuvette advantage but with a closed cuvette inspection condition.

Returning again to FIG. 2B, the present exemplary cuvette 200 includes inlays 240 to reduce the temperature gradients experienced by the saline within the cuvette. The inlays 240 provide for temperature control on a homogenous or homogenizing basis. One of the major disadvantages of static cuvettes is that the heated solution, which is required under the ISO standard varies according to the environment it is contained in. In other words, testing in a cooled environment would effect the closed static cuvette and would cause the conditions to not comply with ISO standards. Additionally, certain polymers that are measured as part of the inspection process are also heat sensitive and will dimensionally vary depending on the temperature. Consequently, the present exemplary cuvette 200 is temperature controlled to maintain a constant standard temperature irrespective of the environment around it.

However, by maintaining a constant temperature via the flow of heated fluid, a temperate gradient may be introduced into the system. The created temperature gradient is often known as a schlieren-effect. A schlieren effect is where a power gradient is shown across a lens under test 270 due to the temperature of the water affecting the lens differently in different areas. Consequently, as illustrated in FIGS. 2A-2F a two tiered system is illustrated providing for the homogenization of the water or saline temperature before it is introduced to the portion of the cuvette housing the lens under test 270. According to one exemplary embodiment, the inlays 240 comprise baffles or mixing plates. The inlays 240 forming a part of the cuvette are configured to break up the laminar flow of the saline from a pump inlet or saline orifice 286 and create a soft mixing effect within the environment of the wet cell itself. Once the saline passes through the inlays 240 and experiences the gentle mixing, a non-laminar flow is produced in order to homogenize the temperature gradients.

According to one exemplary embodiment, the present cuvette 200 also includes a number of positioning features configured to precisely place the cuvette on the cuvette mounting plate 430 of the measurement device 120. According to this exemplary embodiment, the cuvette 200 is positioned such that the lens reception surface of the cuvette 200 is tilted at an approximately five degree orientation 230. In other words, the cuvette 200 is set level. The mounting plate 430 of the measurement device may be tunable for a particular angle to make sure that the lens under inspection 270 is always kept on the tip of the measuring device within the measurement aperture 281 to have a common reference. Due to the tilt 230, the lens under inspection 270 will settle to the plural datum features 283 in the measurement aperture 281 of the cuvette 200 that position it correctly for inspection. Alternatively, the cuvette 200 itself may be manufactured such that the surface of the measurement aperture 281 is positioned at an angle configured to consistently position the lens under inspection 270 against the plural datum features 283 for inspection.

Figure 2A:
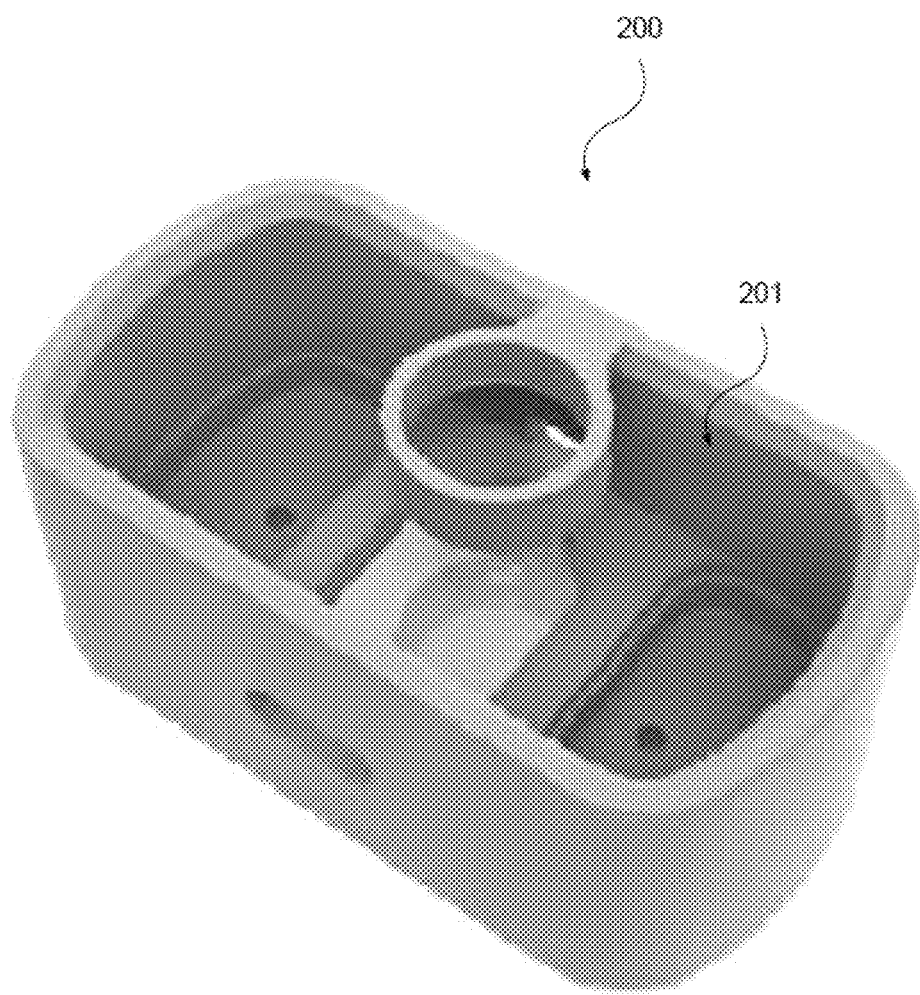
FIGS. 2A-2F illustrate various views of a lens cuvette, according to various embodiments of the present exemplary system and method.
Figure 2B:
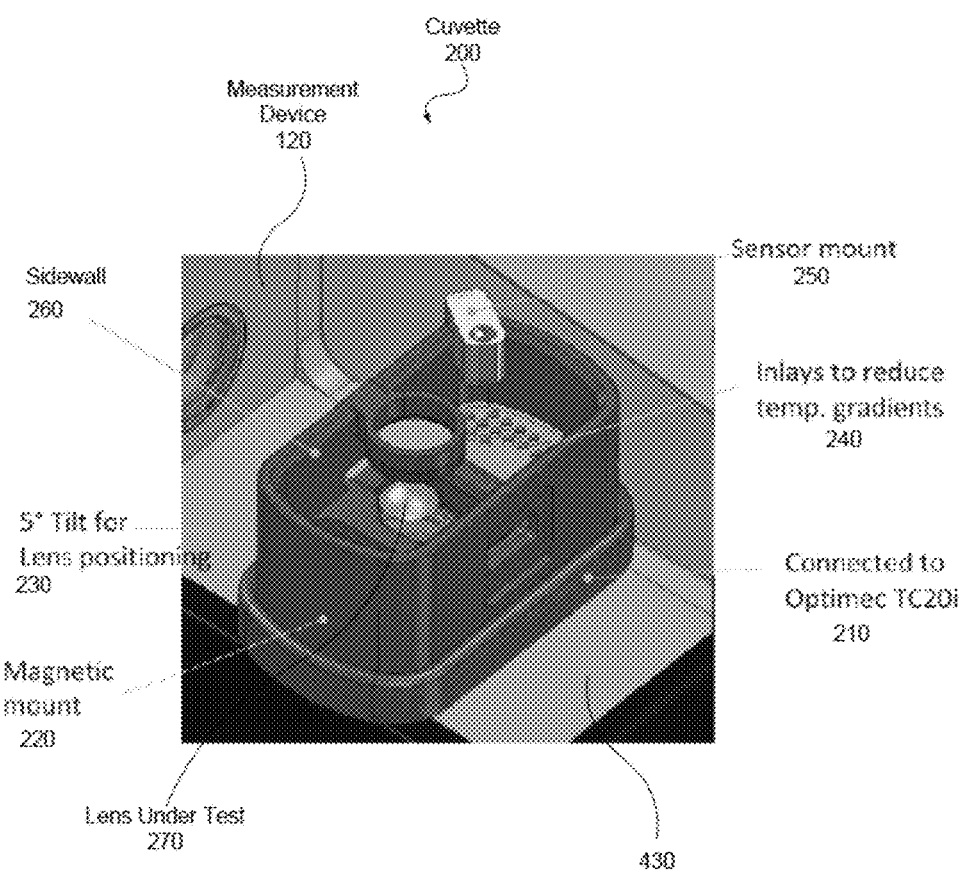
Figure 2C:
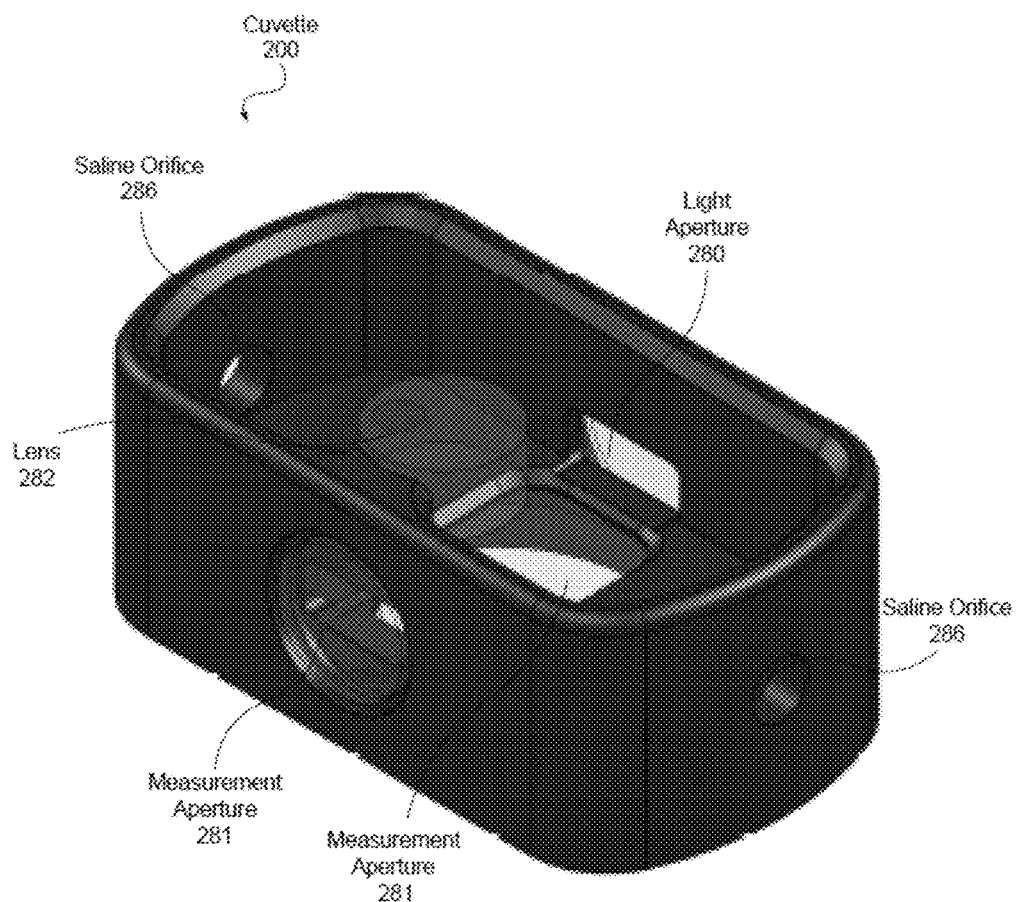
Figure 2D:
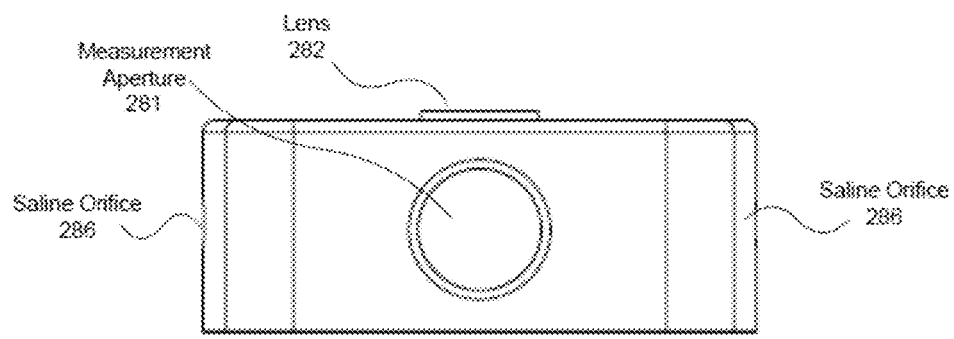
Figure 2E:
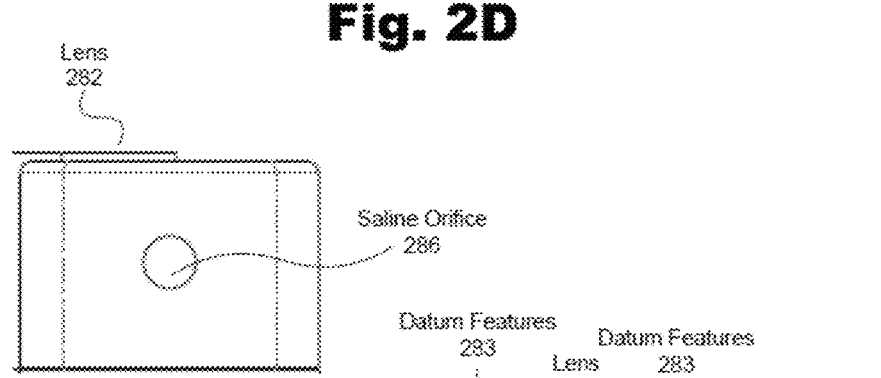
Figure 2F:
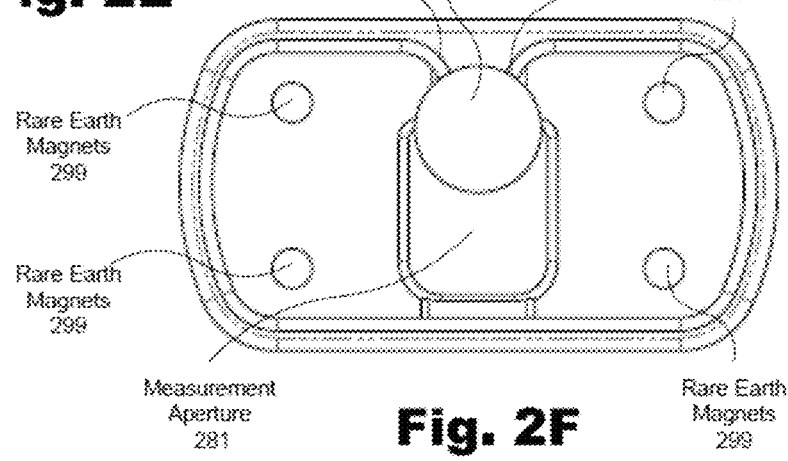
Figure 3:
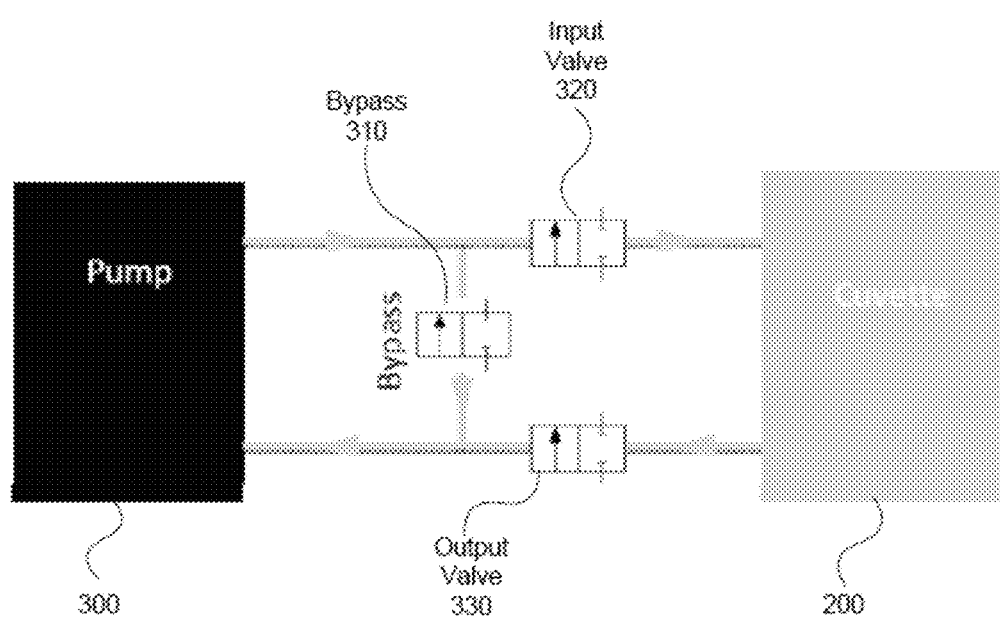
FIG. 3 is a system block diagram illustrating a saline circulation control set-up, according to an embodiment of the present exemplary system and method.

Continuing with FIG. 2f, the cuvette 200 may be fixed to the measurement device 120 by any number of mechanical fastening systems including a magnetic attraction. More specifically, according to one exemplary embodiment one or more rare earth magnets 299 may be formed in either the cuvette 200 and/or the measurement device 120 to facilitate a magnetic fastening of the cuvette 200 to the measurement device. According to one exemplary embodiment illustrated in FIGS. 2b and 2f, a plurality of rare earth magnets 299 may be formed or molded into the cuvette 200. The rare earth magnets 299 may then form a magnetic mount 220 that interacts with a connection base 210 including one or more location pins, datums, or other geometric positioning features that facilitate very accurate and consistent positioning of the cuvette. This magnetic mount 220 also provides for easy removal of the cuvette. Moreover, by molding the rare earth magnets 299 into the cuvette 200, there are no parts or screws such as those utilized in traditional cuvettes that often result in leaks or other structural compromises to the cuvette 200.

Molding of the rare earth magnets 299 into the cuvette 200 to form the magnetic mount 220 is advantageous in that the rare earth magnets are encapsulated and waterproof. This eliminates the likelihood of any rust or contamination. In contrast, traditional cuvettes are fastened with screws and other fasteners that are then sealed with O-rings. The O-rings tend to wear after a time leak.

Once the cuvette 200 is positioned on the magnetic mounts 210 there is absolutely zero movement, according to one exemplary embodiment. Essentially a zero tolerance system is created that locks the cuvette 200 in place. Consequently, during measurement, there is no vibrational effect from the pump 300 or surrounding environment that can be transmitted through the coupling to the cuvette. This allows for the obtaining of a much higher order of inspection accuracy than traditional systems. In order to accurately measure higher order aberrations and accurate powers while judging optical quality, the quality of the process must be very high as well.

Furthermore, the present exemplary cuvette 200 is sterilizable, washable, and replaceable. According to one exemplary embodiment, the cuvette 200 may be made out of one or more appropriate sterilizable materials including, but in no way limited to, a suitable static plastic like ABS or polycarbonate. Furthermore, the various parts of the cuvette 200 itself may be completely opaque, translucent, or transparent, depending on the desired aid to the operator. In contrast, the lens 282 and the measurement aperture 281 that make up the solid part of the cuvette 200, or the top and bottom parallel flats, may be manufactured of glass which is inserted into the cuvette 200 during or after manufacture. The lens 282 and the measurement aperture 281 are manufactured of high quality glass so that the optical reliability, homogeneity, and stability is present.

Measurement Device

Figure 4A:
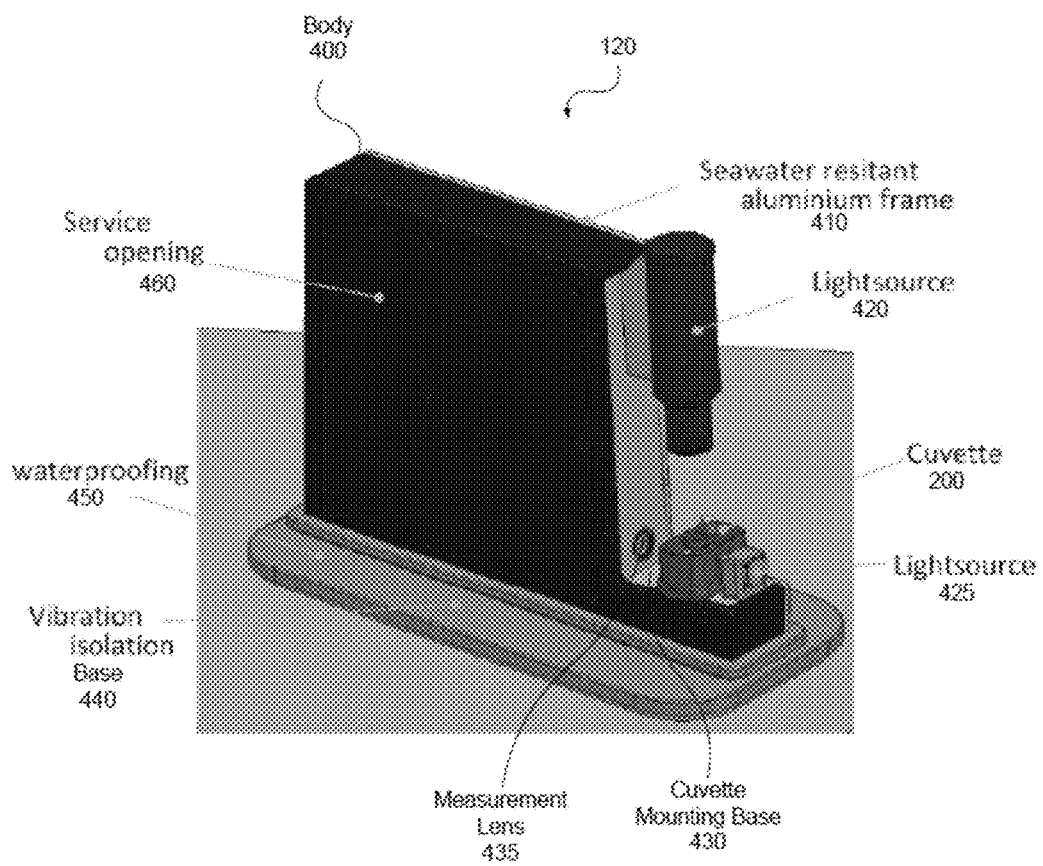
FIGS. 4A and 4B are a perspective view and a cross-sectional perspective view of a measurement device, according to an embodiment of the present exemplary system and method.
Figure 4B:
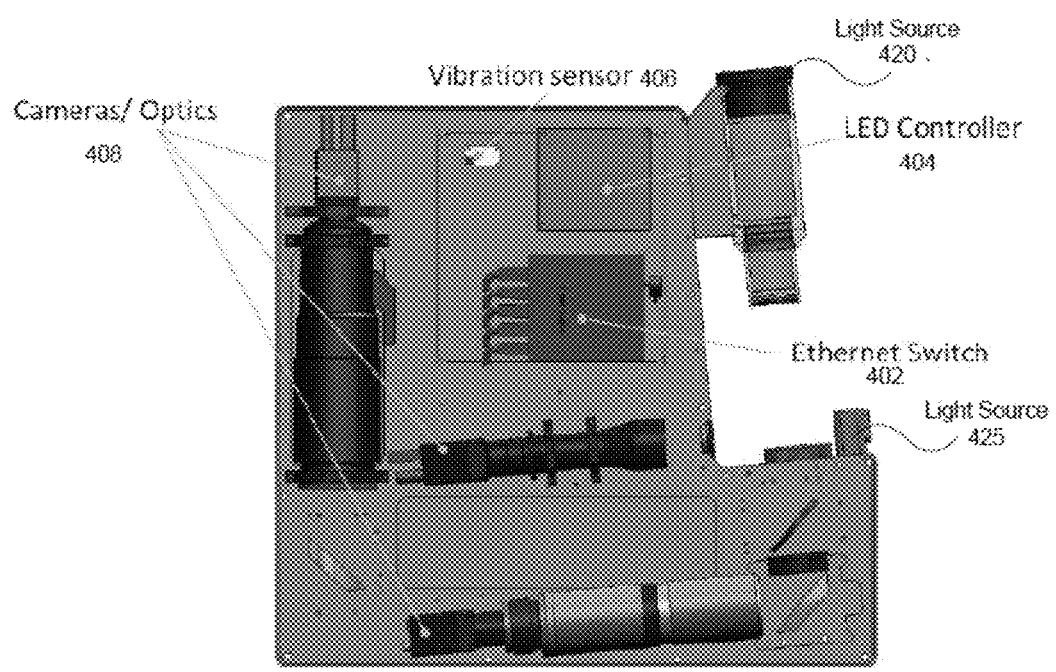

FIGS. 4A and 4B are a perspective view and a cross-sectional perspective view of a measurement device, according to an embodiment of the present exemplary system and method. As illustrated in FIGS. 4A and 4B, the exemplary measurement device 120 includes a main body 400 mounted on a vibration isolating base 440. The vibration isolation base 440 and other components of the measurement device 120 may also be coated by a waterproofing finish 450. As shown, the body 400 defines a cuvette mounting base 430 for receiving and positioning the cuvette 200. A plurality of light sources 420,425 are coupled to the body 400 and specifically positioned to selectively illuminate the lens under test 270 contained in the cuvette 200. Additionally, a number of measurement lenses 435 may be formed in the body 400 of the measurement device 120 to facilitate the capture of lens inspection images. Continuing with FIG. 4A, the exemplary measurement device 120 may include a seawater resistant aluminum frame 410 and a service opening 460 configured to provide structural stability to the measurement device, while enabling service to the internal components of the device.

FIG. 4B illustrates an exemplary internal configuration of the exemplary measurement device 120, according to one exemplary embodiment. As illustrated, the exemplary measurement device 120 may include a vibration sensor 406 configured to sense vibrations experienced by the device for certifying test data, modifying calculations and/or discarding test results. Additionally, an LED controller 404 may be disposed in the measurement device and controllably coupled to the light sources 420,425. According to one exemplary embodiment, the LED controller provides signals to the light sources 420, 425 in order to provide for the desired light fields, as will be described in further detail below.

Additionally, a number of cameras/optics 408 are positioned in the exemplary measurement device 120 to capture images for analysis. Further detail of the exemplary optical configurations are detailed below with reference to FIGS. 6A and 6B.

Figure 5A:
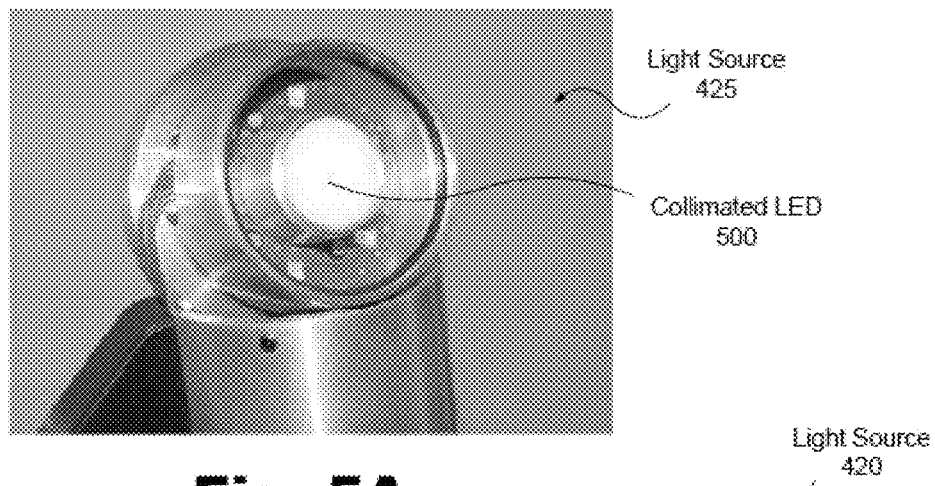
FIGS. 5A and 5B illustrate perspective views of light sources that may be used in connection with the measurement device of FIGS. 4A and 4B, according to an embodiment of the present exemplary system and method.
Figure 5B:
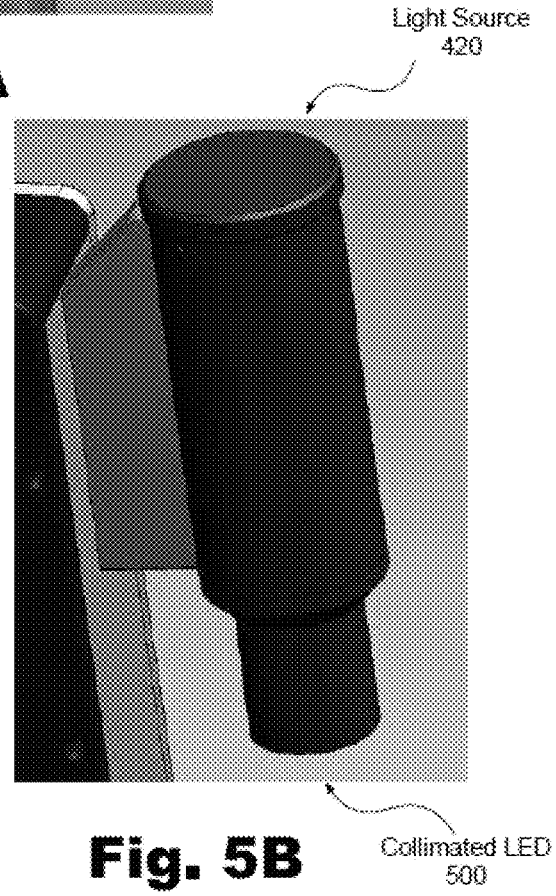

FIGS. 5A and 5B illustrate a number of exemplary light sources 420,425 that may be used in conjunction with the present exemplary system. As illustrated in FIGS. 5A and 5B, collimated LED light sources 500 may be used to generate a desired light field. Alternative light configurations may also be used as are known in the art.

Figure 6A:
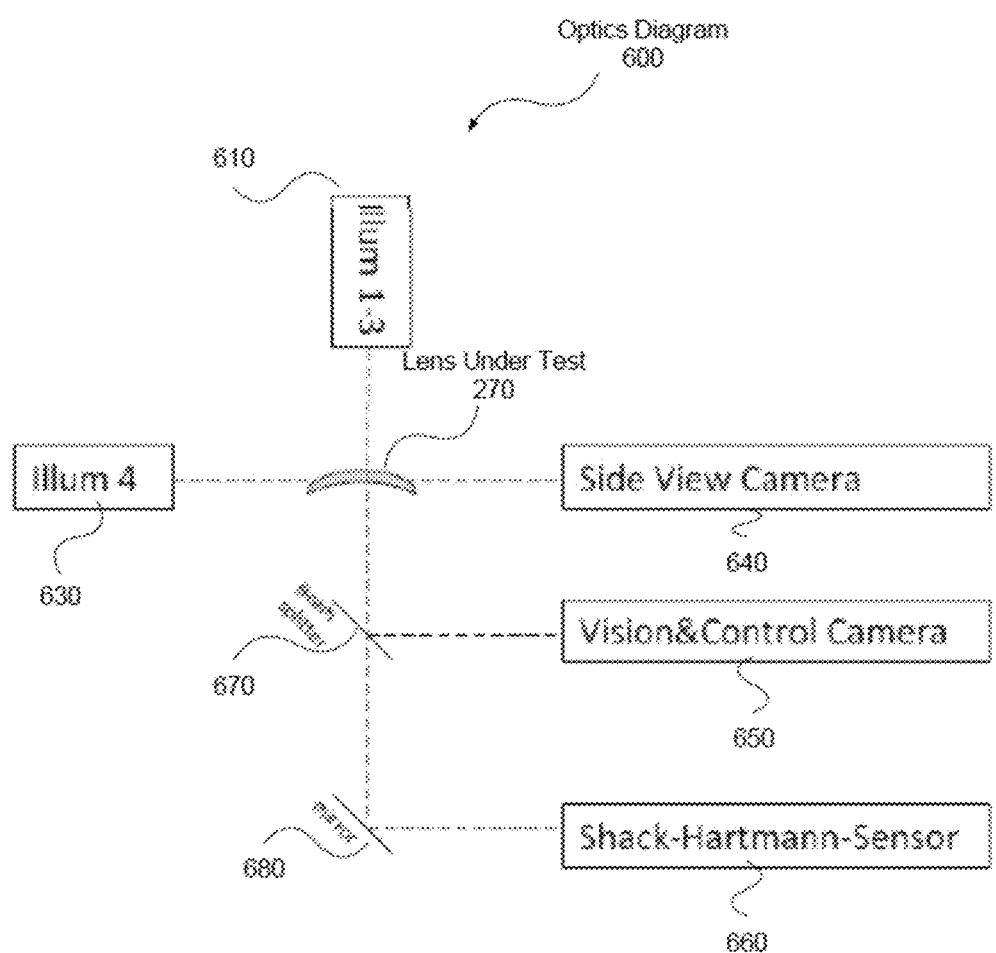
FIGS. 6A and 6B are schematic illustrations of the ophthalmic configuration of the measurement device, according to an embodiment of the present exemplary system and method.
Figure 6B:
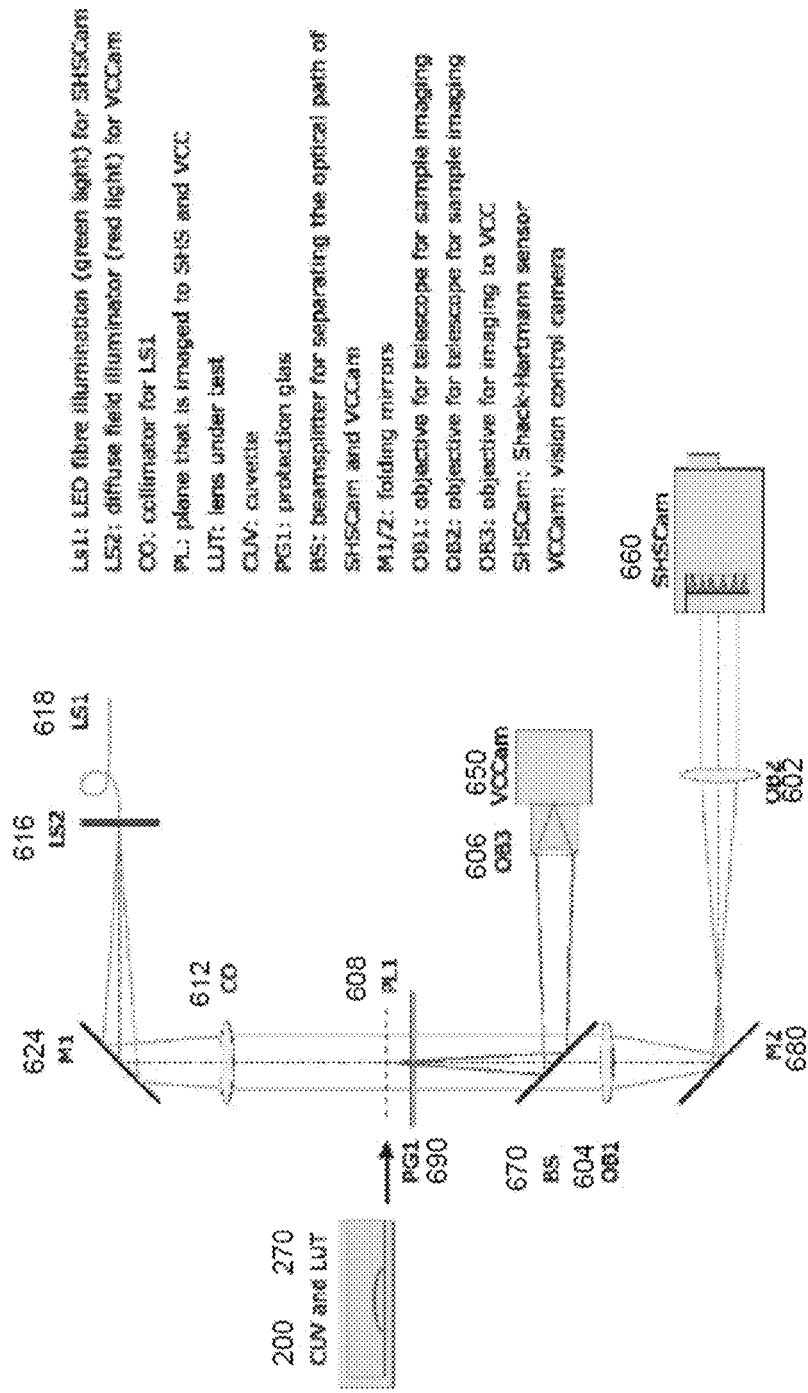

FIGS. 6A and 6B are schematic illustrations of the ophthalmic configuration of the measurement device, according to an embodiment of the present exemplary system and method. As illustrated in the optics diagram 600 of FIG. 6A, any number of illumination sources 610, 630 may be oriented relative to the lens under test 270. According to one exemplary embodiment, one illumination source 630 is configured to provide a light source to a side view camera 640 oriented in line with the lens under test 270 to obtain a side view image of the lens. Additionally, light provided by the various illumination sources 610 oriented in line with the lens under test 270 are reflected and split by any number of mirrors 680 and beam splitters 670 to provide images to the vision and control camera 650 and Shack-Hartman Sensor 660. While one exemplary configuration is illustrated in FIG. 6A, the delivery of the desired images can be performed using any number of varying configurations.

FIG. 6B further illustrates the principles of the present measurement device 120, according to one exemplary embodiment. As illustrated, the cuvette 200 and lens under test 270 may be placed on a protection glass 690 corresponding to a plane 608 that is imaged to the Shack-Hartmann sensor 660 and the vision control camera 650. As shown, the light imaged to the Shack-Hartman sensor 660 and the vision control camera 650 may originate from an LED fiber illumination source 618 and a diffuse field illuminator 616. The light may reflect off any number of mirrors 624, 680, collimators 612, and or beam-splitters 670 in route to the Shack-Hartman sensor 660 and the vision control camera 650. The various elements of the illustrated configuration are specifically oriented to take advantage of the objectives for telescope for sample imaging 604, 602 and the objective for imaging to the VCC 606.

Figure 9A:
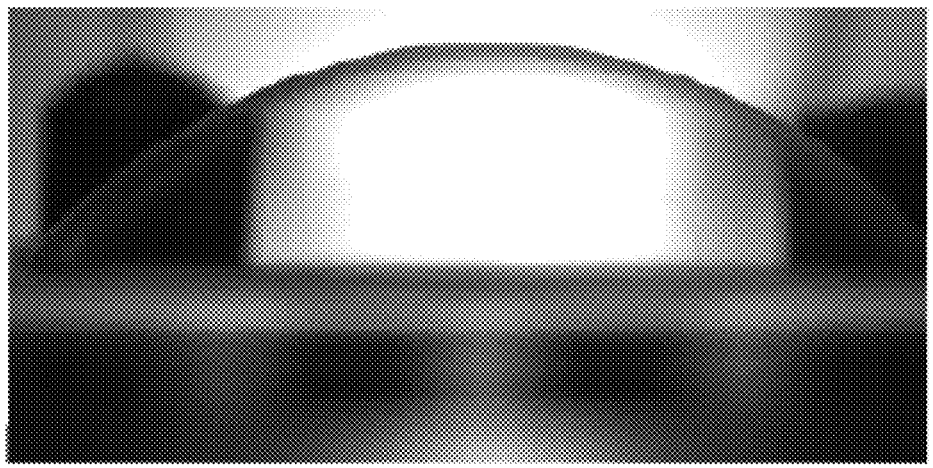
FIGS. 9A and 9B are photographs of a side views of a lens under test, according to an embodiment of the present exemplary system and method.
Figure 9B:
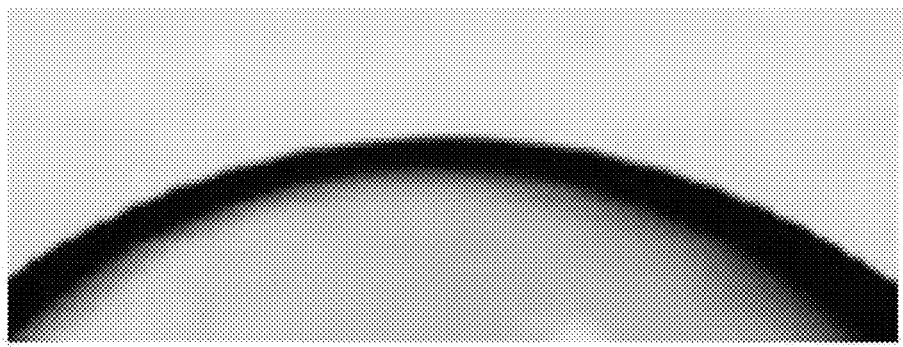

FIGS. 9A and 9B illustrate images taken from a side view camera 640 of the present exemplary system. According to the present exemplary embodiment, the use of a profile or side view camera 640 in conjunction with a Shack-Hartman sensor 660 provides for the identification of power and power shift of the lens under test 270. These measurements are then used to determine the base curve of the lens under test 270. More specifically, using optical profilometry traditionally resulted in diffractive effects at the extremes of the perimeter of the object being measured. Consequently it was impossible to guarantee that you were exactly in the principal meridian of the object being imaged if you're looking across the three dimensional shape in profile. According to the present exemplary system, the height or the maximum height of the lens, or the total sag of the lens 270 is determined by profilometry. The center thickness of the lens 270 from the CT gauge 130 (which is the last measurement) is fed back to the system and is then is subtracted from the front surface maximum height profilometry. The resulting measurement is the back surface total sag from diameter, i.e. from edge to edge to the center, resulting in the overall sag of the lens under test 270. Consequently, the true base curve is determined.

Figure 11:
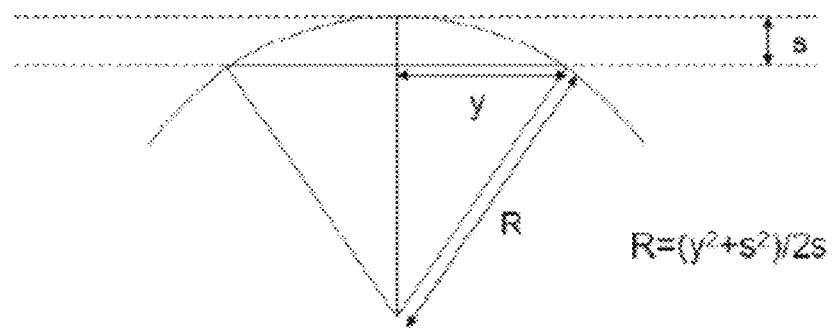
FIG. 11 is a schematic illustrating the base-curve measuring principles used by the present measurement device, according to an embodiment of the present exemplary system and method.

This determination of the true base curve is beneficial because the industry works on a standard of 10 mm cord and measures to a spherical form. However, these traditional measurements are not ideal if an aspheric lens, bicurve lens, or multiple curve lens is manufactured. According to these embodiments, accurate base curve cannot be measured. Specifically, traditional measuring configurations include a probe that is rotated upwards until it touches the bottom of the lens while the lens is supported on a 10 mm cord. Once the probe contacts the lens, a dial gauge then estimates the base curve. The actual formula traditionally used is S=R minus the square route of $R^2$ minus $Y^2$ where $Y^2$ is a half cord and R is the radius of the aptical radius, as illustrated in FIG. 11. However, traditional base curve computations fail to take into account aspheric lenses.

In contrast to traditional systems, the present exemplary system uses the back total sag determined through front surface profilometry and subtraction of the measured CT, which is accurate to half a micron. With this information, we can determine the power of the lens because the Shack-Hartmann sensor 660 traces the power. Knowing what the base curve should read with the measured power, along with the CT and the overall sag base curve can be determined relative to what the actual power turns out to be based on the calculateable relationship between power and front and back curve.

Once the power, the overall sag of the front and back, and the CT are determined, the deviation between the back and the front of the lens can be determined in order to achieve the identified power as measured with the Shack-Hartmann sensor.

Confirmation of the base curve can then be determined by comparing the overall sag of the lens with what the base curve should be reading. Comparison of the two will provide a very accurate confirmation on the base curve. In other words, the present exemplary system provides a very accurate trace across a 10 mm section of the lens using front surface profilometry.

Light Field

Figure 7A:
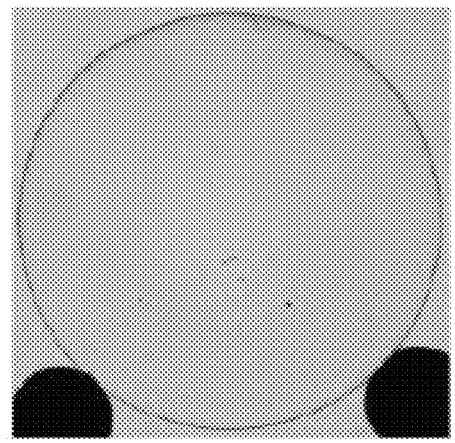
FIGS. 7A, 7B, and 7C are photographs of a defect inspection image using a bright field light field, a telecentric light field, and a dark field light field, respectively, according to an embodiment of the present exemplary system and method.
Figure 7B:
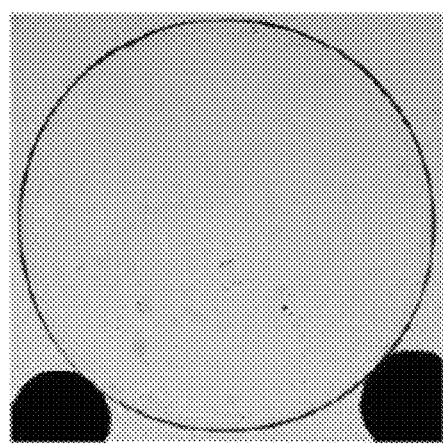
Figure 7C:
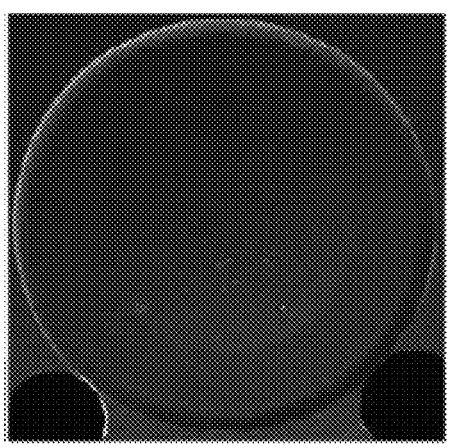

According to the present exemplary system, at least three distinct light fields are used and imaged to the user 150 during inspection of a lens under test 270. FIGS. 7A, 7B, and 7C are photographs of a defect inspection image using a bright field light field, a telecentric light field, and a dark field light field, respectively, according to an embodiment of the present exemplary system and method.

According to the present exemplary system, a bright field light field works from the premise that normal surface defects and inclusions are displayed, according to standard inspection systems. This lighting condition is good for very broad based rejects and for determining whether something is a reject or merely a contaminant on the lens under test 270.

The second light field, illustrated in FIG. 7B, is a telecentric light field. A telecentric light field basically extends the focal lens of the light as it comes through the lens system, creating a much greater depth of field or three dimensional effect when compared to the lens of a bright field. Consequently, non-wet circles or bubbles passing through the lens will be displayed by the telecentric light field as deep or profound tunnels. The resulting three dimensional appearances highlight the non-wet defects that are only displayed as a light circle by the bright field light field.

The dark field illustrated in FIG. 7C, which is a black background, is essentially a light source which is coming in from behind the lens in an oblique direction that, therefore, creates a negative image of the lens which highlights edge splits.

The various light fields are sequentially presented to the user 150 on the pen display 110 for human detection of defects. The defects can then be circled or identified by the human user 150 so that they system may then measure and quantify the defect.

The present exemplary system also incorporates a color based iron filter that is configured to automatically identify rust contamination.

Figure 8:
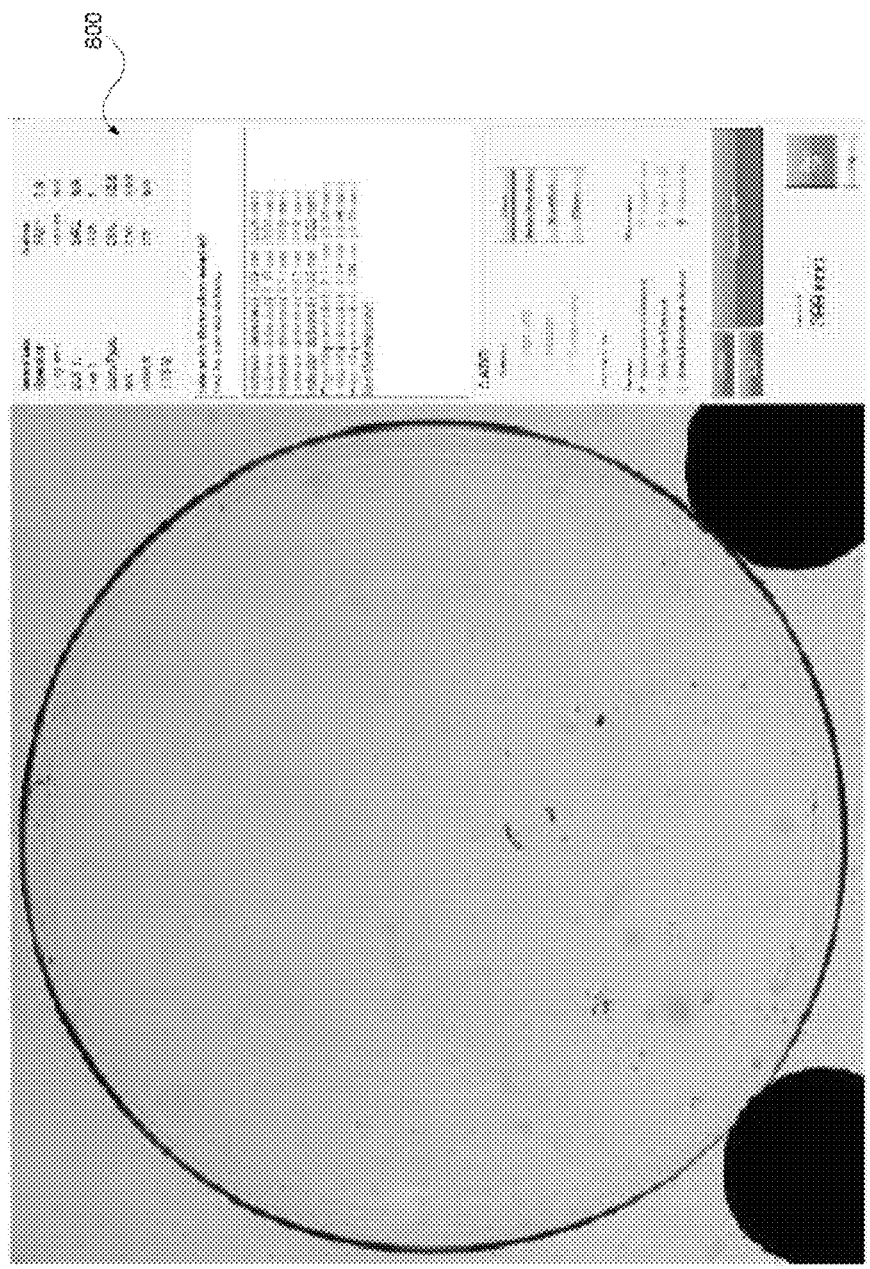
FIG. 8 is a screen shot of a lens inspection image lighted against a telecentric light field and its corresponding test data, according to an embodiment of the present exemplary system and method.

FIG. 8 is a screen shot of a lens inspection image lighted against a telecentric light field and its corresponding test data, according to an embodiment of the present exemplary system and method. As mentioned previously, the lens inspection image is presented to the user 150 for identification of actual lens defects, as contrasted with dust or other impurities that may appear in the image. As illustrated in FIG. 8, once the actual lens defects are identified, the system quantifies the size and severity of the defects and displays the automated results as test data 800 to the user 150.

CT Measurement Device

Figure 10A:
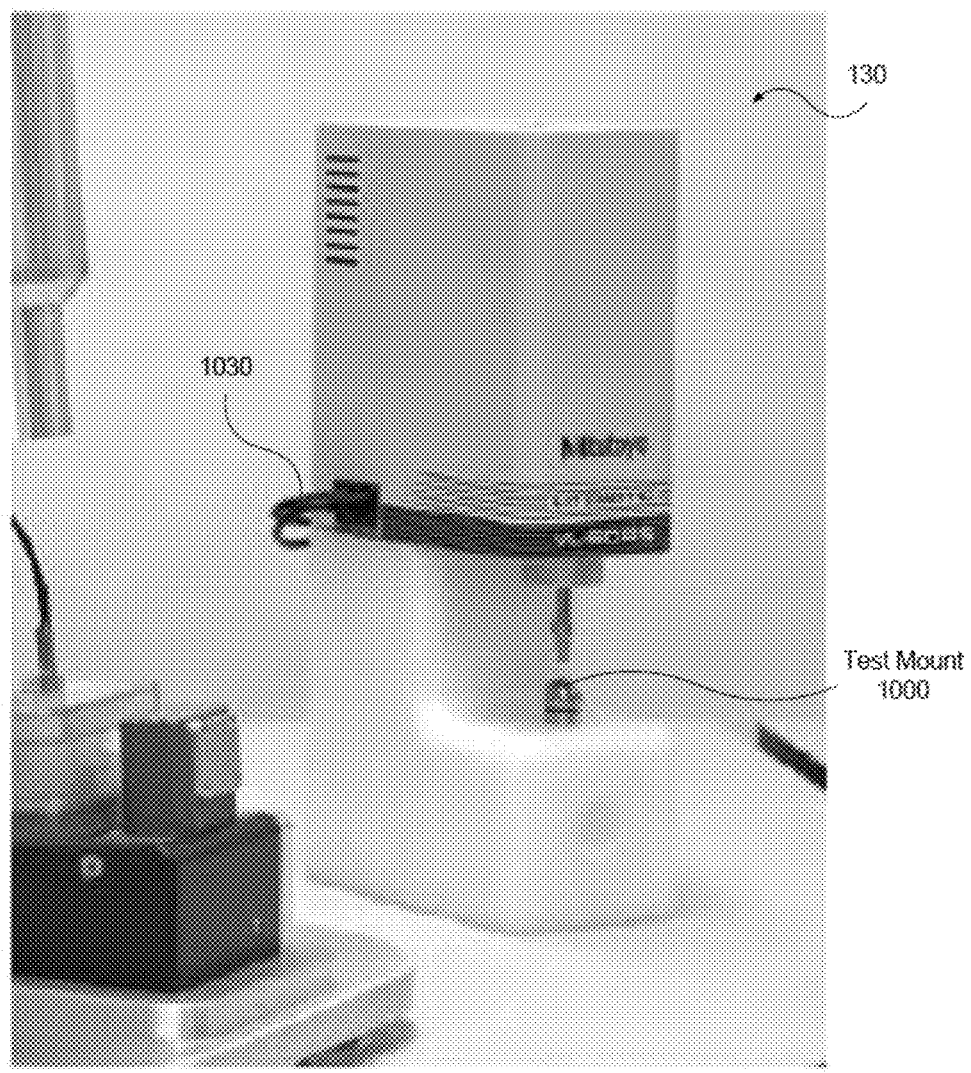
FIGS. 10A and 10B are perspective views and frontal views of a CT measurement device, according to an embodiment of the present exemplary system and method.
Figure 10B:
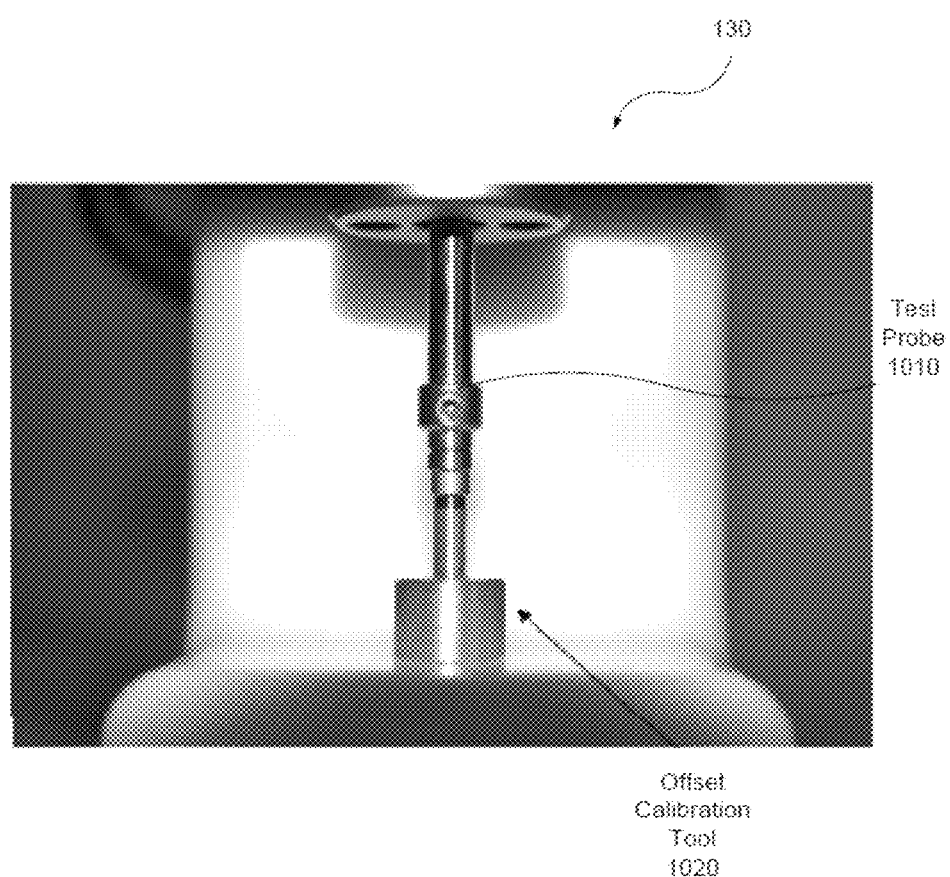

FIGS. 10A and 10B are perspective views and frontal views of a CT measurement device, according to an embodiment of the present exemplary system and method. According to one exemplary embodiment, the exemplary CT gauge 130 includes a test mount 1000 for receiving a lens under test 270 after all other inspections have been completed. According to this exemplary embodiment, the CT gauge 130 includes a test probe 1010 that is synchronized with an offset calibration tool 1020 to provide accurate measurements. As noted above, the CT results are transmitted from the CT gauge 130 to the measurement device 120 via a communication cable 1030 or other data transmission medium. The CT measurements for the lens under test 270 may then be subtracted from the front surface maximum height profilometry to determine the overall sag of the lens under test 270.

User Interface

Figure 12A:
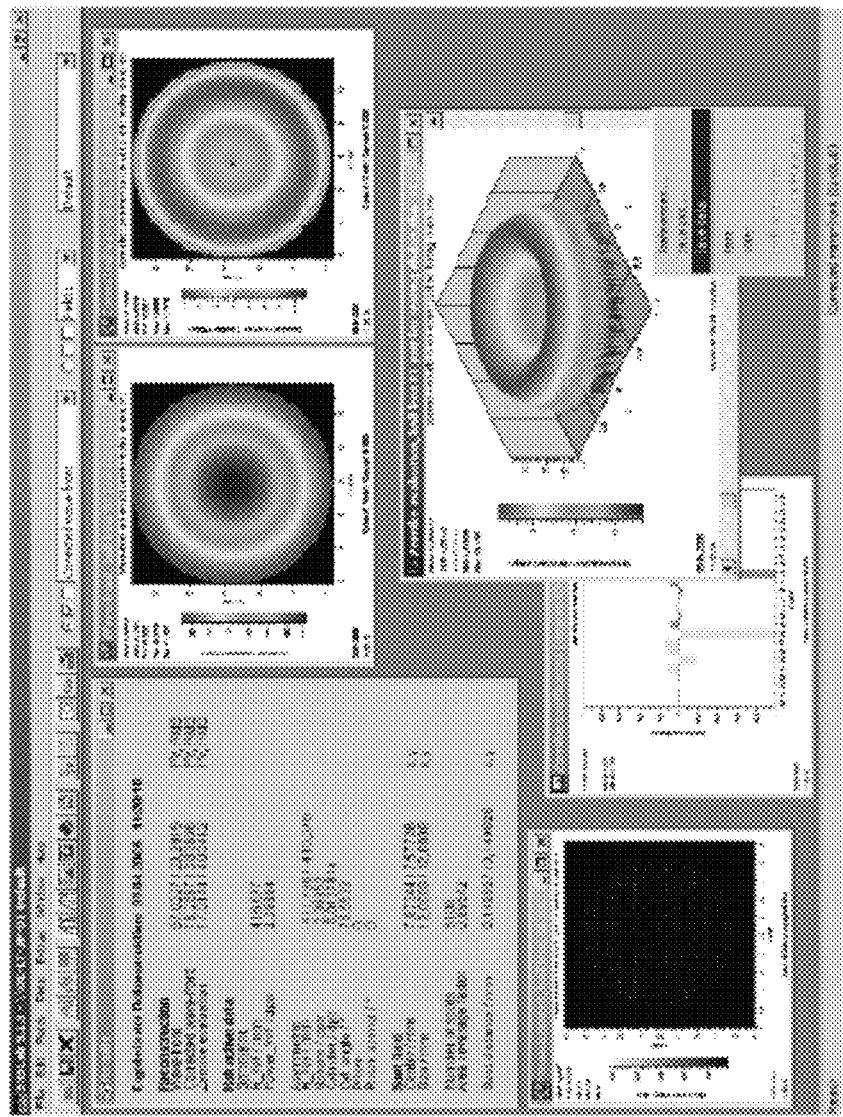
FIG. 12A is a screen shot of lens inspection data obtained with the present lens inspection system, according to an embodiment of the present exemplary system and method.
Figure 12B:
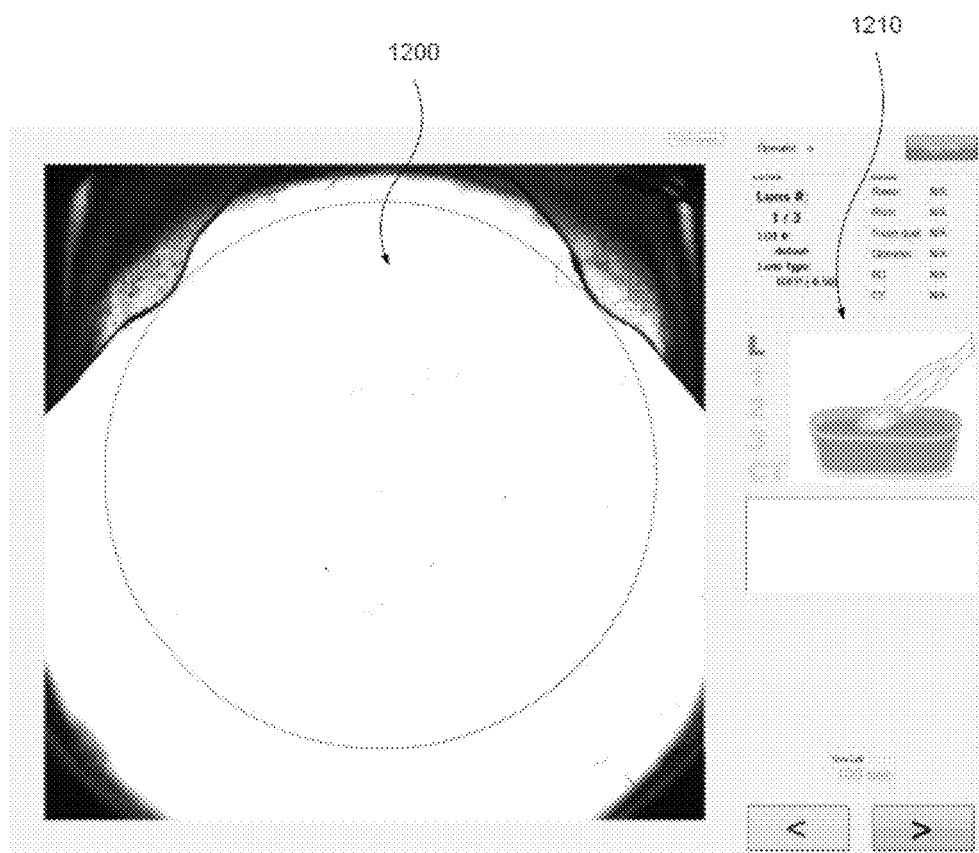
FIG. 12B is a screen shot of a lens inspection image and the corresponding test procedure instructions, according to an embodiment of the present exemplary system and method.

As mentioned previously, the present exemplary system 100 may include a pen display 110 for displaying images to a user 150 and for allowing interaction between the user 150 and the system. The pen display 110 of the present exemplary system 100 may include any number of data display and/or input devices including, but in no way limited to a touch display, a pen display, and the like. The pen display 110 provides a human interface having a touch screen that displays test images, test data (FIG. 12A), provides step by step directions, video, and visual imagery configured to show the operator how to perform proper inspection. Specifically, as illustrated in FIG. 12B, the user 150 is provided with a test image 1200 and a corresponding step by step instructions 1210 on how to obtain the desired inspection information. The step by step instructions 1210 may be in the form of video, images, sounds, and the like. This enables the present exemplary system to enable rapid competency by users 150 regardless of language, training, or other communication barriers.

Additionally, the visual step by step instructions 1210 enable the incorporation of customized voiceover of the imagery or instructions which may be provided in a choice of different languages so that the instructions are tailored to the individual 150 that is using the measuring system 100. Consequently, training time will be reduced and language requirements may be eliminated. Additionally, productivity will be enhanced due to rapid training and understanding.

Figure 13A:
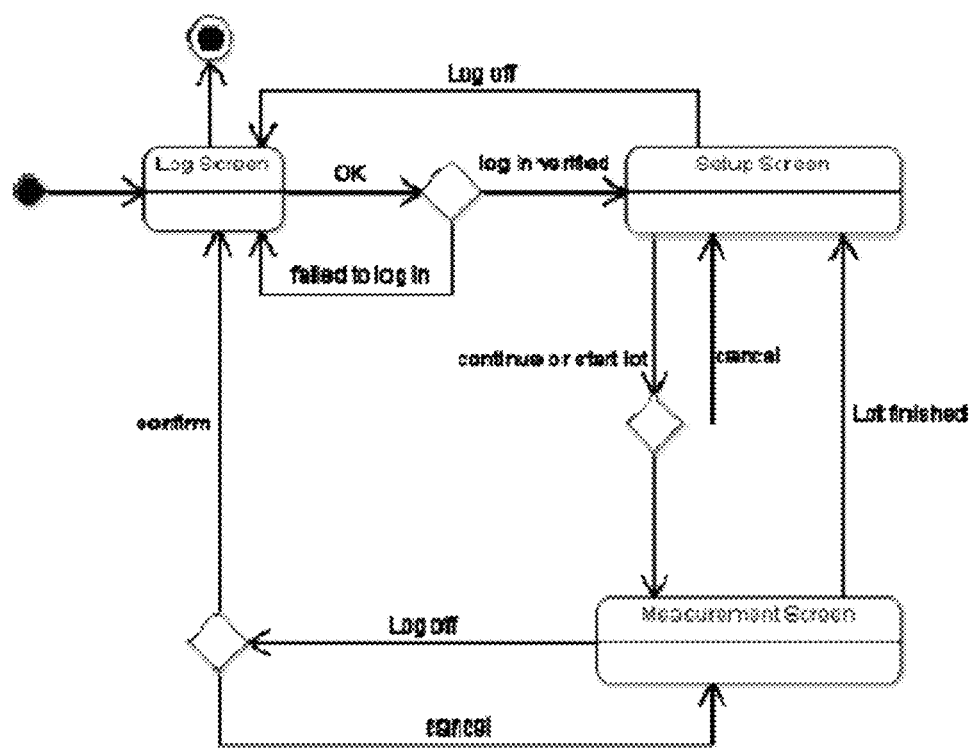
FIG. 13A is a schematic illustrating the step-by-step workflow screen generation incorporated by the lens inspection system, according to an embodiment of the present exemplary system and method.
Figure 13B:
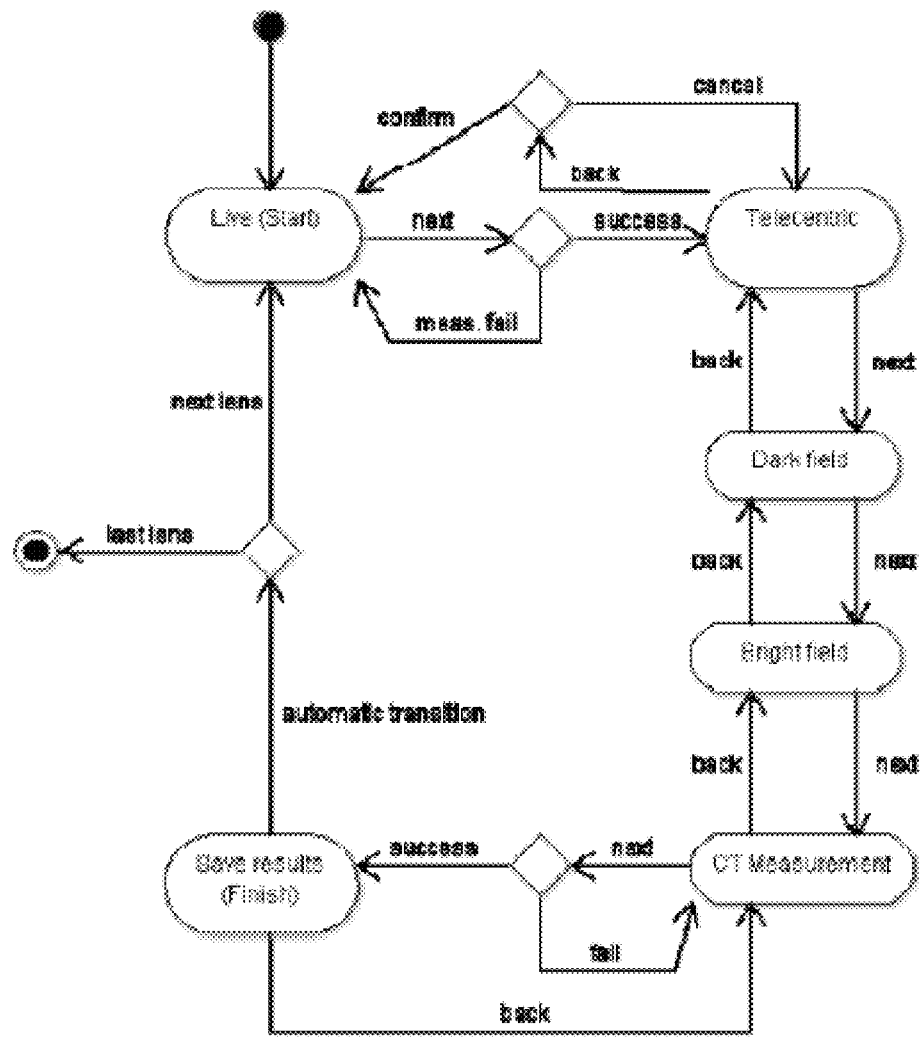
FIG. 13B is a schematic illustrating the step-by-step workflow of a lens inspection incorporated by the present lens inspection system, according to an embodiment of the present exemplary system and method.
Figure 13C:
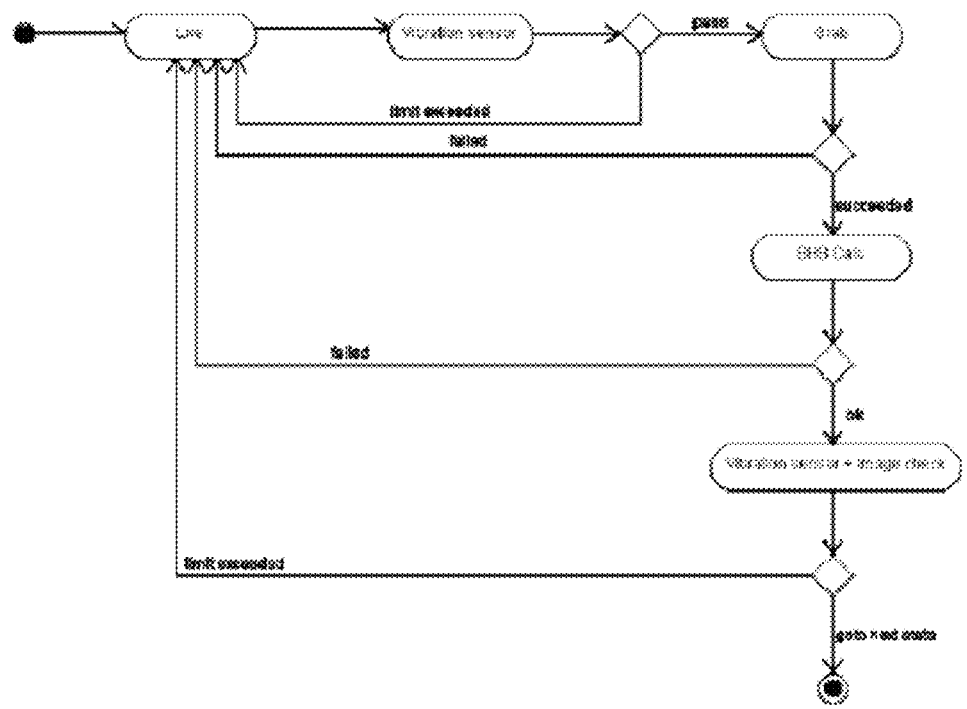
FIG. 13C is a schematic illustrating the step-by-step workflow for lens measurement incorporated by the lens inspection system, according to an embodiment of the present exemplary system and method.

FIG. 13A is a schematic illustrating the step-by-step workflow screen generation incorporated by the lens inspection system, according to an embodiment of the present exemplary system and method. As illustrated, the user 150 is directed in a step-wise fashion to perform a log on, a set up, and a measurement. Similarly, FIG. 13B is a schematic illustrating the step-by-step workflow of a lens inspection incorporated by the present lens inspection system, according to an embodiment of the present exemplary system and method. As illustrated, the user 150 is systematically stepped through the inspection process including the display of a telecentric light field image, a dark field image, and a bright field image (in any sequential order) followed by a CT measurement. Similarly, as illustrated in the step-by-step workflow for lens measurement incorporated by the lens inspection system shown in FIG. 13C, environmental conditions such as vibrations are measured and calculations are performed and/or rejected according to identified limits.

FIG. 14 depicts a block diagram of a computer system 1510 suitable for implementing the present systems and methods, either as an integral component of the measurement device 120, or as a stand-alone component communicatively coupled to the inspection system 100. Computer system 1510 includes a bus 1512 which interconnects major subsystems of computer system 1510, such as a central processor 1514, a system memory 1517 (typically RAM, but which may also include ROM, flash RAM, or the like), an input/output controller 1518, an external audio device, such as a speaker system 1520 via an audio output interface 1522, an external device, such as a display screen 1524 via display adapter 1526, serial ports 1528 and 1530, a keyboard 1532 (interfaced with a keyboard controller 1533), multiple USB devices 1592 (interfaced with a USB controller 1590), a storage interface 1534, a floppy disk drive 1537 operative to receive a floppy disk 1538, a host bus adapter (HBA) interface card 1535A operative to connect with a Fibre Channel network 1590, a host bus adapter (HBA) interface card 1535B operative to connect to a SCSI bus 1539, and an optical disk drive 1540 operative to receive an optical disk 1542. Also included are a mouse 1546 (or other point-and-click device, coupled to bus 1512 via serial port 1528), a modem 1547 (coupled to bus 1512 via serial port 1530), and a network interface 1548 (coupled directly to bus 1512).

Bus 1512 allows data communication between central processor 1514 and system memory 1517, which may include read-only memory (ROM) or flash memory (neither shown), and random access memory (RAM) (not shown), as previously noted. The RAM is generally the main memory into which the operating system and application programs are loaded. The ROM or flash memory can contain, among other code, the Basic Input-Output system (BIOS) which controls basic hardware operation such as the interaction with peripheral components or devices. For example, the ATA system 170 to implement the present systems and methods may be stored within the system memory 1517. Applications resident with computer system 1510 are generally stored on and accessed via a computer readable medium, such as a hard disk drive (e.g., fixed disk 1544), an optical drive (e.g., optical drive 1540), a floppy disk unit 1537, or other storage medium. Additionally, applications can be in the form of electronic signals modulated in accordance with the application and data communication technology when accessed via network modem 1547 or interface 1548.

Storage interface 1534, as with the other storage interfaces of computer system 1510, can connect to a standard computer readable medium for storage and/or retrieval of information, such as a fixed disk drive 1544. Fixed disk drive 1544 may be a part of computer system 1510 or may be separate and accessed through other interface systems. Modem 1547 may provide a direct connection to a remote server via a telephone link or to the Internet via an internet service provider (ISP). Network interface 1548 may provide a direct connection to a remote server via a direct network link to the Internet via a POP (point of presence). Network interface 1548 may provide such connection using wireless techniques, including digital cellular telephone connection, Cellular Digital Packet Data (CDPD) connection, digital satellite data connection or the like.

Many other devices or subsystems (not shown) may be connected in a similar manner (e.g., document scanners, digital cameras and so on). Conversely, all of the devices shown in FIG. 15 need not be present to practice the present systems and methods. The devices and subsystems can be interconnected in different ways from that shown in FIG. 15. The operation of a computer system such as that shown in FIG. 15 is readily known in the art and is not discussed in detail in this application. Code to implement the present disclosure can be stored in computer-readable medium such as one or more of system memory 1517, fixed disk 1544, optical disk 1542, or floppy disk 1538. The operating system provided on computer system 1510 may be MS-DOS®, MS-WINDOWS®, OS/2®, UNIX®, Linux®, or another known operating system.

Moreover, regarding the signals described herein, those skilled in the art will recognize that a signal can be directly transmitted from a first block to a second block, or a signal can be modified (e.g., amplified, attenuated, delayed, latched, buffered, inverted, filtered, or otherwise modified) between the blocks. Although the signals of the above described embodiment are characterized as transmitted from one block to the next, other embodiments of the present systems and methods may include modified signals in place of such directly transmitted signals as long as the informational and/or functional aspect of the signal is transmitted between blocks. To some extent, a signal input at a second block can be conceptualized as a second signal derived from a first signal output from a first block due to physical limitations of the circuitry involved (e.g., there will inevitably be some attenuation and delay). Therefore, as used herein, a second signal derived from a first signal includes the first signal or any modifications to the first signal, whether due to circuit limitations or due to passage through other circuit elements which do not change the informational and/or final functional aspect of the first signal.

INDUSTRIAL APPLICABILITY

According to the present exemplary systems and methods, a single apparatus is provided for inspecting and determining quality of ophthalmic products, such as contact lenses. As noted above, the user is not tasked with making the final call on whether the lens under test will pass or fail. Rather, the user is far more accurate in determining subtleties about rejects, i.e. determining whether a potential reject is an actual reject or merely a contaminant or other issue in the system. For example, a small hair or a small particle or a small piece of fluff may enter the saline and seep to the surface of the lens under test. A human user can easily make the identification that the potential defect is merely a contaminant due to the special nature of that kind of reject on the surface of the lens and the fact that the human can manipulate the lens with a pair of tweezers in the cuvette.

However, human users are not reliable at measuring a reject against a known standard. Rather, human users typically introduce some form of a bias in the determination, such as an inter-personnel bias and intra-personnel bias, resulting in inconsistent results. In other words, the user can make different decisions on different days, depending on whether they slept well the night before or whether they have an emotional problem, etc. Consequently, there typically differences between different people about what they inspect and what results they get.

Therefore, the present system allows for human identification of actual defects and the system then quantifies the defects. In other words, the human user qualifies the instrument, qualifies the reject via identification, and then the computer measures the defect according to a fixed standard based on preprogrammed algorithms. Consequently, the human user never makes a judgment on the pass or fail applicability of that reject. According to one embodiment, the user identifies a defect that then simply draw a circle or other identifier generally around that reject. The system processor will identify the reject within that drawn circle and will immediately put an overlay over that reject which is going to exactly conform to the input that the company has put for that reject to whether the defect complies within the company or ISO standards. Therefore, every defect that is circled in that category will be subjected to a common overlay so that there is no subjectivity in the quantification of defects.

According to one exemplary embodiment, an individual company may provide baseline standards for acceptability of defects, which are then implemented by the present system after an overlay of the defects. Consequently, the present system provides a completely objective construction of whether a lens under test passes or fails and all lenses are judged on a set of agreed criteria, which may or may not be the ISO standards.

Similarly, depending on magnification, limits for pass or failure of a lens may be set by a company incorporating the present system. The limits will establish what constitutes a reject. The incorporation of a user determination will reduce or eliminate the occurrence of false rejects.

Furthermore, in contrast to traditional systems, the present exemplary system provides a one-step automatic measurement system. Once the lens under test is set up in the cuvette and the user is satisfied that there not sufficient imperfections to constitute a reject, a first button may be pressed and the power and other ISO parameters are determined automatically.

The preceding description has been presented only to illustrate and describe embodiments and examples of the principles described. This description is not intended to be exhaustive or to limit these principles to any precise form disclosed. Many modifications and variations are possible in light of the above teaching.

The invention claimed is:
1. A contact lens inspection system, comprising:
a processor;

a memory component communicatively coupled to the processor;

an optical inspection device communicatively coupled to the processor, wherein the optical inspection device includes a cuvette;

a center thickness (CT) measurement device communicatively coupled to the processor; and a visual display communicatively coupled to the processor;

wherein the processor quantifies defects of a contact lens according to a predetermined standard by overlaying the defect when the defects are identified to evaluate whether the defect conforms with the predetermined standard; and wherein the cuvette further comprises a fully wet cuvette, the cuvette including a cuvette positioning and retention system configured to couple the cuvette to the optical inspection device.

2. The contact lens inspection system of claim 1, wherein the cuvette positioning and retention system further comprises a mounting plate formed on the optical inspection device.

3. The contact lens inspection system of claim 2, wherein the mounting plate formed on the optical inspection device comprises a surface exhibiting at least a 5 degree tilt relative to horizontal when the optical inspection device is disposed on a level surface.

4. The contact lens inspection system of claim 1, wherein the cuvette further comprises:

a cuvette body including a plurality of side walls defining an interior volume;

a closed base coupled to the plurality of side walls, wherein the closed base includes a magnetic mount;

a plurality of saline orifices defined by the plurality of side walls;

a horizontal inlay disposed in the interior volume above the plurality of saline orifices; and a measurement aperture formed in the interior volume above the horizontal inlays.

5. The contact lens inspection system of claim 4, wherein the cuvette further comprises at least one light aperture formed in a first side wall and an opposing measurement aperture formed in an opposing side wall.

6. The contact lens inspection system of claim 4, wherein the cuvette further comprises:

a sensor mount formed on at least one of the side walls;

a plurality of baffles or mixing plates associated with the horizontal inlay; and at least one lens positioning feature disposed on the measurement aperture.

7. The contact lens inspection system of claim 4, wherein the cuvette further comprises an input valve fluidly coupled to a first of the plurality of saline orifices and an output valve fluidly coupled to a second of the plurality of saline orifices.

8. The contact lens inspection system of claim 4, further comprising a saline pump system fluidly coupled to the cuvette;

wherein the saline pump system further comprises:

a saline pump fluidly coupled to the input valve and the output valve;

a filter; and a bypass disposed between the saline pump and the input and output valves;

wherein the bypass is configured to be selectively actuated when measurements are taken within the cuvette.

9. The contact lens inspection system of claim 4, wherein the cuvette further comprises an anti-Schlieren control and a vibration and pulse control.

10. The contact lens inspection system of claim 1, wherein the optical inspection device further comprises:

a main body including a cuvette mounting base;

a vibration isolating base;

at least one light source positioned to selectively illuminate a lens under test disposed in the cuvette when mounted on the cuvette mounting base; and at least one camera disposed on the main body.

11. The contact lens inspection system of claim 10, wherein the at least one light source comprises at least one light emitting diode (LED).

12. The contact lens inspection system of claim 10, wherein the at least one camera further comprises a side view camera and a vision and control camera.

13. The contact lens inspection system of claim 10, further comprising: a Shack-Hartmann sensor;

and a beam splitter disposed opposite the second light source, a first output of the beam splitter being directed to the vision and control camera and a second output of the beam splitter being directed to the Shack Hartman sensor.

14. The contact lens inspection system of claim 13, wherein the inspection system is configured to image a lens under test in at least 3 distinct light fields.

15. A contact lens inspection system, comprising:

a processor; a memory component communicatively coupled to the processor;

an optical inspection device communicatively coupled to the processor, wherein the optical inspection device includes a cuvette; a center thickness (CT) measurement device communicatively coupled to the processor; and a visual display communicatively coupled to the processor; wherein the processor quantifies defects of a contact lens and compares the quantified defects to a predetermined standard when the defects are identified; and wherein the cuvette further comprises a cuvette positioning and retention system configured to couple the cuvette to the optical inspection device;

wherein the optical inspection device further comprises a main body including a cuvette mounting base, a vibration isolating base, at least one light source positioned to selectively illuminate a lens under test disposed in the cuvette when mounted on the cuvette mounting base, and at least one camera disposed on the main body, a Shack-Hartmann sensor, and a beam splitter disposed opposite the second light source, a first output of the beam splitter being directed to the vision and control camera and a second output of the beam splitter being directed to the Shack Hartman sensor;

wherein the inspection system is configured to image a lens under test in at least 3 distinct light fields;

wherein the at least 3 distinct light field images are a bright field light field, a telecentric light field, and a dark field light field.

16. The contact lens inspection system of claim 1, wherein the processor is configured to determine a sagittal height of a lens under test using profilometry.

17. The contact lens inspection system of claim 1, further comprising a color interpretation module.

18. The contact lens inspection system of claim 1, wherein the system incorporates both human and automated qualification.

19. The contact lens inspection system of claim 1, wherein said memory includes code, which, when accessed by the processor, causes the processor to display step-by-step workflow instructions to a user on the visual display;

wherein the step-by-step workflow instructions to a user on the visual display are free of spoken or written language based instructions.

\* \* \* \* \*